US012065482B2

(12) United States Patent
Lee et al.

(10) Patent No.: US 12,065,482 B2
(45) Date of Patent: Aug. 20, 2024

(54) STABLE LIQUID PHARMACEUTICAL FORMULATION OF ANTI-INFLUENZA VIRUS ANTIBODY

(71) Applicant: Celltrion Inc., Incheon (KR)

(72) Inventors: Joon Won Lee, Incheon (KR); Won Yong Han, Incheon (KR); Su Jung Kim, Incheon (KR); Jun Seok Oh, Incheon (KR); So Young Kim, Incheon (KR); Kwang Woo Kim, Incheon (KR); Yeon Kyeong Shin, Incheon (KR)

(73) Assignee: Celltrion Inc., Incheon (KR)

( * ) Notice: Subject to any disclaimer, the term of this patent is extended or adjusted under 35 U.S.C. 154(b) by 695 days.

(21) Appl. No.: 16/324,364

(22) PCT Filed: Aug. 9, 2017

(86) PCT No.: PCT/KR2017/008605
§ 371 (c)(1),
(2) Date: Feb. 8, 2019

(87) PCT Pub. No.: WO2018/030777
PCT Pub. Date: Feb. 15, 2018

(65) Prior Publication Data
US 2021/0347861 A1  Nov. 11, 2021

(30) Foreign Application Priority Data

Aug. 10, 2016 (KR) .................. 10-2016-0101719

(51) Int. Cl.
*A61K 39/395* (2006.01)
*A61K 9/00* (2006.01)
*A61K 47/10* (2017.01)
*A61K 47/18* (2017.01)
*A61K 47/26* (2006.01)
*A61P 31/16* (2006.01)
*C07K 16/10* (2006.01)
*A61K 39/00* (2006.01)

(52) U.S. Cl.
CPC ........ *C07K 16/1018* (2013.01); *A61K 9/0019* (2013.01); *A61K 39/39591* (2013.01); *A61K 47/10* (2013.01); *A61K 47/183* (2013.01); *A61K 47/26* (2013.01); *A61P 31/16* (2018.01); A61K 2039/507 (2013.01); A61K 2039/545 (2013.01); C07K 2317/56 (2013.01); C07K 2317/565 (2013.01); C07K 2317/94 (2013.01)

(58) Field of Classification Search
None
See application file for complete search history.

(56) References Cited

U.S. PATENT DOCUMENTS

| 4,861,335 | A | 8/1989 | Reynolds |
| 5,085,642 | A | 2/1992 | Sarnoff et al. |
| 5,681,291 | A | 10/1997 | Galli |
| 6,331,174 | B1 | 12/2001 | Reinhard et al. |
| 9,573,991 | B2 * | 2/2017 | Chang ..................... A61P 31/16 |
| 9,856,312 | B2 * | 1/2018 | Chang ............. G01N 33/56983 |
| 10,703,802 | B2 * | 7/2020 | Hong ..................... A61K 31/13 |
| 2008/0086280 | A1 | 4/2008 | Baumgarte |
| 2008/0286280 | A1 | 11/2008 | Kallmeyer et al. |
| 2010/0086555 | A1 * | 4/2010 | Lanzavecchia ......... A61P 31/12 424/159.1 |
| 2013/0289246 | A1 | 10/2013 | Crowe et al. |
| 2016/0052997 | A1 | 2/2016 | Hong et al. |

FOREIGN PATENT DOCUMENTS

| KR | 10-2014-0119641 A | 10/2014 |
| KR | 10-2015-0024301 A | 3/2015 |
| KR | 10-2016-0068946 | 6/2016 |
| WO | 2007/006939 A2 | 1/2007 |
| WO | 2011/111966 A2 | 9/2011 |
| WO | 2011/161226 A2 | 12/2011 |
| WO | 2013/174936 A1 | 11/2013 |
| WO | 2018/030777 A1 | 2/2018 |

OTHER PUBLICATIONS

International Written Opinion for International Application No. PCT/KR2017/008605, mailed on Nov. 20, 2017, 13 pages with English Translation.
International Preliminary Report on Patentability received for PCT Patent Application No. PCT/KR2017/008605, mailed on Feb. 21, 2019, 16 pages with English Translation.
PCT International Search Report, PCT/KR2017/008605, mailing date Nov. 20, 2017, with English translation.
Kabat et al. Sequences of Proteins of Immunological Interest (5th), U.S. Department of Health and Human Services, Public Health Service, National Institutes of Health, Bethesda, MD. (Jan. 1991).
Amorij et al "Development of Stable Influenza Vaccine Powder Formulations: Challenges and Possibilities" Pharmaceutical Research, vol. 25, No. 6 (Jun. 2008) pp. 1256-1273.

(Continued)

*Primary Examiner* — Yunsoo Kim
(74) *Attorney, Agent, or Firm* — TraskBritt

(57) ABSTRACT

A stable liquid pharmaceutical preparation of an anti-influenza virus antibody and, more specifically, a stable liquid pharmaceutical preparation that comprises: (A) an anti-influenza virus antibody or a mixture of two or more different types of anti-influenza virus antibodies; (B) a surfactant; (C) a sugar or a sugar derivative; and (D) an amino acid. The stable liquid pharmaceutical preparation for an anti-influenza virus antibody disclosed herein has excellent storage stability at low temperature (5° C.), room temperature (25° C.), and high temperature (40° C.) and excellent long-term (12 months) storage stability, and may be administered intravenously, intramuscularly, transdermally, subcutaneously, intraperitoneally, topically, or in combinations thereof.

9 Claims, No Drawings

Specification includes a Sequence Listing.

(56) References Cited

OTHER PUBLICATIONS

Anonymous: "Vaccine Excipient & Media Summary" Last retrieved May 17, 2022 from http://www.cdc.gov/vaccines/pubs/pinkbook/downloads/appendices/b/excipient-table-2.pdf.
Anonymous: "Vaccine Excipient & Media Summary", 2013, XP055153211.
Chinese First Office Action for Chinese Application No. 201780062284.9, dated Nov. 24, 2020, 11 pages with translation.
Chinese Second Office Action for Chinese Application No. 201780062284.9, dated Jul. 13, 2021, 6 pages with translation.
European Communication pursuant to Article 94(3) EPC for European Application No. 17839795, dated May 10, 2022, 3 pages.
European Extended Search Report and Opinion for European Application No. 17839795.6, dated Oct. 16, 2019, 8 pages.
European Search Report and Search Opinion Received for EP Application No. 17839795, dated on Oct. 23, 2019, 7 pages.

* cited by examiner

SEQUENCE LISTING

```
<160> NUMBER OF SEQ ID NOS: 140

<210> SEQ ID NO 1
<211> LENGTH: 11
<212> TYPE: PRT
<213> ORGANISM: Artificial Sequence
<220> FEATURE:
<223> OTHER INFORMATION: Antibody 1 light chain CDR1

<400> SEQUENCE: 1

Arg Ala Ser Glu Asn Ile Trp Asn Asn Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Antibody 1 light chain CDR2

<400> SEQUENCE: 2

Gly Ala Ser Thr Gly Ala Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Antibody 1 light chain CDR3

<400> SEQUENCE: 3

Gln Gln Tyr Asn Ser Trp Pro Arg Thr
1               5
```

-continued

```
<210> SEQ ID NO 4
<211> LENGTH: 5
<212> TYPE: PRT
<213> ORGANISM: Artificial Sequence
<220> FEATURE:
<223> OTHER INFORMATION: Antibody 1 heavy chain CDR1

<400> SEQUENCE: 4

Ser His Ala Ile Ser
1               5

<210> SEQ ID NO 5
<211> LENGTH: 17
<212> TYPE: PRT
<213> ORGANISM: Artificial Sequence
<220> FEATURE:
<223> OTHER INFORMATION: Antibody 1 heavy chain CDR2

<400> SEQUENCE: 5

Gly Ile Ser Pro Met Phe Gly Thr Thr His Tyr Ala Gln Lys Phe Gln
1               5                   10                  15

Gly

<210> SEQ ID NO 6
<211> LENGTH: 14
<212> TYPE: PRT
<213> ORGANISM: Artificial Sequence
<220> FEATURE:
<223> OTHER INFORMATION: Antibody 1 heavy chain CDR3

<400> SEQUENCE: 6

Asp Gly Ala Gly Ser Tyr Tyr Pro Leu Asn Trp Phe Asp Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Antibody 2 light chain CDR1

<400> SEQUENCE: 7

Arg Ala Ser His Arg Val Gly Ser Thr Tyr Ile Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Antibody 2 light chain CDR2

<400> SEQUENCE: 8

Gly Ala Ser Asn Arg Ala Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Antibody 2 light chain CDR3

<400> SEQUENCE: 9

Gln Gln Phe Ser Val Ser Pro Trp Thr
1               5
```

<210> SEQ ID NO 10
<211> LENGTH: 5
<212> TYPE: PRT
<213> ORGANISM: Artificial Sequence
<220> FEATURE:
<223> OTHER INFORMATION: Antibody 2 heavy chain CDR1

<400> SEQUENCE: 10

Thr Tyr Gly Val Ser
1               5

<210> SEQ ID NO 11
<211> LENGTH: 17
<212> TYPE: PRT
<213> ORGANISM: Artificial Sequence
<220> FEATURE:
<223> OTHER INFORMATION: Antibody 2 heavy chain CDR2

<400> SEQUENCE: 11

Trp Ile Ser Ala Tyr Thr Gly Ile Thr Asp Tyr Ala Gln Lys Phe Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Antibody 2 heavy chain CDR3

<400> SEQUENCE: 12

Asp Lys Val Gln Gly Arg Val Glu Val Gly Ser Gly Arg His Asp
1               5                   10                  15

Tyr

<210> SEQ ID NO 13
<211> LENGTH: 12
<212> TYPE: PRT
<213> ORGANISM: Artificial Sequence
<220> FEATURE:
<223> OTHER INFORMATION: Antibody 3 light chain CDR1

<400> SEQUENCE: 13

Arg Ala Ser Gln Ser Leu Ser Ser Ser Ser Leu Val
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Antibody 3 light chain CDR2

<400> SEQUENCE: 14

Gly Ala Ser Ser Arg Ala Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Antibody 3 light chain CDR3

<400> SEQUENCE: 15

Gln Gln Tyr Gly Asn Ser Pro Tyr Thr
1               5

<210> SEQ ID NO 16
<211> LENGTH: 6
<212> TYPE: PRT
<213> ORGANISM: Artificial Sequence
<220> FEATURE:
<223> OTHER INFORMATION: Antibody 3 heavy chain CDR1

<400> SEQUENCE: 16

Asn Asn Tyr Ala Ile Ser
1               5

<210> SEQ ID NO 17
<211> LENGTH: 18
<212> TYPE: PRT
<213> ORGANISM: Artificial Sequence
<220> FEATURE:
<223> OTHER INFORMATION: Antibody 3 heavy chain CDR2

<400> SEQUENCE: 17

Gly Gly Ile Ser Pro Ile Phe Gly Thr Leu Asn Tyr Ala Glu Arg Phe
1               5                   10                  15

Gln Gly

<210> SEQ ID NO 18
<211> LENGTH: 11
<212> TYPE: PRT
<213> ORGANISM: Artificial Sequence
<220> FEATURE:
<223> OTHER INFORMATION: Antibody 3 heavy chain CDR3

<400> SEQUENCE: 18

Gly Cys Gly Tyr Asn Cys Tyr Tyr Phe Asp Gly
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Antibody 4 light chain CDR1

<400> SEQUENCE: 19

Arg Ala Ser Gln Ser Val Ser Ile Ser Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Antibody 4 light chain CDR2

<400> SEQUENCE: 20

Gly Ala Ser Arg Arg Ala Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Antibody 4 light chain CDR3

<400> SEQUENCE: 21

```
Gln Gln Tyr Gly Ser Ser Pro Tyr Thr
1               5

<210> SEQ ID NO 22
<211> LENGTH: 5
<212> TYPE: PRT
<213> ORGANISM: Artificial Sequence
<220> FEATURE:
<223> OTHER INFORMATION: Antibody 4 heavy chain CDR1

<400> SEQUENCE: 22

Arg Phe Gly Ile His
1               5

<210> SEQ ID NO 23
<211> LENGTH: 17
<212> TYPE: PRT
<213> ORGANISM: Artificial Sequence
<220> FEATURE:
<223> OTHER INFORMATION: Antibody 4 heavy chain CDR2

<400> SEQUENCE: 23

Val Ile Trp Tyr Asp Gly Ser Asn Lys Phe Tyr Ala Asp Ser Val Lys
1               5                   10                  15

Gly

<210> SEQ ID NO 24
<211> LENGTH: 18
<212> TYPE: PRT
<213> ORGANISM: Artificial Sequence
<220> FEATURE:
<223> OTHER INFORMATION: Antibody 4 heavy chain CDR3

<400> SEQUENCE: 24

Asp Ser Arg Gly Tyr Cys Ser Ser Ile Ile Cys Phe Glu Gly Gly Leu
1               5                   10                  15

Asp Asn

<210> SEQ ID NO 25
<211> LENGTH: 12
<212> TYPE: PRT
<213> ORGANISM: Artificial Sequence
<220> FEATURE:
<223> OTHER INFORMATION: Antibody 5 light chain CDR1

<400> SEQUENCE: 25

Arg Ala Ser Arg Arg Val Gly Ser Thr Tyr Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Antibody 5 light chain CDR2

<400> SEQUENCE: 26

Gly Ala Ser Ser Arg Ala Ala
1               5

<210> SEQ ID NO 27
<211> LENGTH: 9
<212> TYPE: PRT
<213> ORGANISM: Artificial Sequence
<220> FEATURE:
```

<223> OTHER INFORMATION: Antibody 5 light chain CDR3

<400> SEQUENCE: 27

Gln Gln Tyr Ala Ala Ser Pro Trp Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Antibody 5 heavy chain CDR1

<400> SEQUENCE: 28

Thr Tyr Gly Ile Ser
1               5

<210> SEQ ID NO 29
<211> LENGTH: 17
<212> TYPE: PRT
<213> ORGANISM: Artificial Sequence
<220> FEATURE:
<223> OTHER INFORMATION: Antibody 5 heavy chain CDR2

<400> SEQUENCE: 29

Trp Ile Ser Ala Tyr Thr Gly Asn Thr Asp Tyr Ala Gln Lys Val Gln
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Antibody 5 heavy chain CDR3

<400> SEQUENCE: 30

Asp Lys Val Gln Gly Arg Val Glu Ala Gly Ser Gly Gly Arg His Asp
1               5                   10                  15

Tyr

<210> SEQ ID NO 31
<211> LENGTH: 12
<212> TYPE: PRT
<213> ORGANISM: Artificial Sequence
<220> FEATURE:
<223> OTHER INFORMATION: Antibody 6 light chain CDR1

<400> SEQUENCE: 31

Arg Ala Ser His Ser Val Gly Ser Thr Tyr Ile Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Antibody 6 light chain CDR2

<400> SEQUENCE: 32

Gly Ala Ser Asn Arg Ala Thr
1               5

<210> SEQ ID NO 33
<211> LENGTH: 9

```
<212> TYPE: PRT
<213> ORGANISM: Artificial Sequence
<220> FEATURE:
<223> OTHER INFORMATION: Antibody 6 light chain CDR3

<400> SEQUENCE: 33

Gln Gln Phe Ser Val Ser Pro Trp Thr
1               5

<210> SEQ ID NO 34
<211> LENGTH: 5
<212> TYPE: PRT
<213> ORGANISM: Artificial Sequence
<220> FEATURE:
<223> OTHER INFORMATION: Antibody 6 heavy chain CDR1

<400> SEQUENCE: 34

Thr Tyr Gly Val Ser
1               5

<210> SEQ ID NO 35
<211> LENGTH: 17
<212> TYPE: PRT
<213> ORGANISM: Artificial Sequence
<220> FEATURE:
<223> OTHER INFORMATION: Antibody 6 heavy chain CDR2

<400> SEQUENCE: 35

Trp Ile Ser Gly Tyr Thr Gly Ile Thr Asp Tyr Ala Gln Lys Ser Gln
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Antibody 6 heavy chain CDR3

<400> SEQUENCE: 36

Asp Lys Val Gln Gly Arg Val Glu Ala Gly Ser Gly Gly Arg His Asp
1               5                   10                  15

Tyr

<210> SEQ ID NO 37
<211> LENGTH: 12
<212> TYPE: PRT
<213> ORGANISM: Artificial Sequence
<220> FEATURE:
<223> OTHER INFORMATION: Antibody 7 light chain CDR1

<400> SEQUENCE: 37

Arg Ala Ser His Ser Ile Gly Ser Thr Tyr Ile Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Antibody 7 light chain CDR2

<400> SEQUENCE: 38

Gly Ala Ser Asn Arg Ala Ser
1               5
```

<210> SEQ ID NO 39
<211> LENGTH: 9
<212> TYPE: PRT
<213> ORGANISM: Artificial Sequence
<220> FEATURE:
<223> OTHER INFORMATION: Antibody 7 light chain CDR3

<400> SEQUENCE: 39

Gln Gln Phe Ser Val Ser Pro Trp Thr
1               5

<210> SEQ ID NO 40
<211> LENGTH: 5
<212> TYPE: PRT
<213> ORGANISM: Artificial Sequence
<220> FEATURE:
<223> OTHER INFORMATION: Antibody 7 heavy chain CDR1

<400> SEQUENCE: 40

Thr Tyr Gly Val Ser
1               5

<210> SEQ ID NO 41
<211> LENGTH: 17
<212> TYPE: PRT
<213> ORGANISM: Artificial Sequence
<220> FEATURE:
<223> OTHER INFORMATION: Antibody 7 heavy chain CDR2

<400> SEQUENCE: 41

Trp Ile Ser Gly Tyr Thr Gly Ile Thr Asp Tyr Ala Gln Lys Phe Gln
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: Antibody 7 heavy chain CDR3

<400> SEQUENCE: 42

Asp Lys Val Gln Gly Arg Val Glu Val Gly Ser Gly Gly Arg His Asp
1               5                   10                  15

Tyr

<210> SEQ ID NO 43
<211> LENGTH: 127
<212> TYPE: PRT
<213> ORGANISM: Artificial Sequence
<220> FEATURE:
<223> OTHER INFORMATION: Antibody 1 light chain variable region

<400> SEQUENCE: 43

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Glu Asn
            35                  40                  45

Ile Trp Asn Asn Leu Ala Trp Tyr Gln Gln Lys Pro Gly Gln Ala Pro
        50                  55                  60

Arg Leu Leu Ile Ser Gly Ala Ser Thr Gly Ala Thr Gly Val Pro Ser

```
                65                  70                  75                  80
Arg Phe Arg Gly Ser Gly Ser Arg Thr Glu Phe Thr Leu Thr Ile Ser
                    85                  90                  95

Ser Leu Gln Ser Glu Asp Phe Ala Ile Tyr Phe Cys Gln Gln Tyr Asn
                    100                 105                 110

Ser Trp Pro Arg Thr Phe Gly Pro Gly Thr Lys Val Glu Ile Lys
            115                 120                 125
```

<210> SEQ ID NO 44
<211> LENGTH: 142
<212> TYPE: PRT
<213> ORGANISM: Artificial Sequence
<220> FEATURE:
<223> OTHER INFORMATION: Antibody 1 heavy chain variable region

<400> SEQUENCE: 44

```
Met Asp Trp Thr Trp Arg Phe Leu Phe Val Ala Ala Ala Thr Gly
1               5                   10                  15

Val Gln Cys Gln Val Gln Leu Val Gln Ser Gly Ala Glu Val Lys Met
                20                  25                  30

Pro Gly Ser Ser Val Lys Val Ser Cys Lys Thr Ser Gly Val Phe Phe
            35                  40                  45

Ser Ser His Ala Ile Ser Trp Val Arg Gln Ala Pro Gly Gln Gly Leu
        50                  55                  60

Glu Trp Met Gly Gly Ile Ser Pro Met Phe Gly Thr Thr His Tyr Ala
65                  70                  75                  80

Gln Lys Phe Gln Gly Arg Val Thr Ile Thr Ala Asp Gln Ser Thr Thr
                85                  90                  95

Thr Ala Tyr Met Glu Leu Thr Ser Leu Thr Ser Glu Asp Thr Ala Val
                100                 105                 110

Tyr Tyr Cys Ala Arg Asp Gly Ala Gly Ser Tyr Tyr Pro Leu Asn Trp
            115                 120                 125

Phe Asp Pro Trp Gly Gln Gly Thr Leu Val Thr Val Ser Ser
        130                 135                 140
```

<210> SEQ ID NO 45
<211> LENGTH: 108
<212> TYPE: PRT
<213> ORGANISM: Artificial Sequence
<220> FEATURE:
<223> OTHER INFORMATION: Antibody 2 light chain variable region

<400> SEQUENCE: 45

```
Glu Val Val Leu Thr Gln Ser Pro Gly Thr Leu Ala Leu Pro Pro Gly
1               5                   10                  15

Glu Arg Ala Thr Leu Ser Cys Arg Ala Ser His Arg Val Gly Ser Thr
                20                  25                  30

Tyr Ile Ala Trp Tyr Gln Gln Lys Ser Gly Gln Ala Pro Arg Arg Leu
            35                  40                  45

Ile Tyr Gly Ala Ser Asn Arg Ala Thr Asp Ile Pro Asp Arg Phe Ser
        50                  55                  60

Gly Ser Gly Ser Gly Thr Asp Phe Thr Leu Thr Ile Arg Arg Leu Glu
65                  70                  75                  80

Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys
                100                 105
```

```
<210> SEQ ID NO 46
<211> LENGTH: 126
<212> TYPE: PRT
<213> ORGANISM: Artificial Sequence
<220> FEATURE:
<223> OTHER INFORMATION: Antibody 2 heavy chain variable region

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Pro Glu Trp Val
        35                  40                  45

Gly Trp Ile Ser Ala Tyr Thr Gly Ile Thr Asp Tyr Ala Gln Lys Phe
    50                  55                  60

Gln Gly Arg Val Thr Leu Thr Thr Asp Ala Thr Thr Ala Thr Ala Phe
65                  70                  75                  80

Leu Asp Leu Arg Ser Leu Arg Pro Asp Asp Thr Ala Thr Tyr Phe Cys
                85                  90                  95

Ala Arg Asp Lys Val Gln Gly Val Glu Val Gly Ser Gly Gly Arg
            100                 105                 110

His Asp Tyr Trp Gly Gln Gly Thr Leu Val Ile Val Ser Ser
        115                 120                 125

<210> SEQ ID NO 47
<211> LENGTH: 128
<212> TYPE: PRT
<213> ORGANISM: Artificial Sequence
<220> FEATURE:
<223> OTHER INFORMATION: Antibody 3 light chain variable region

<400> SEQUENCE: 47

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Leu Ser Ser Ser Leu Val Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Asn Ser Pro Tyr Thr Phe Gly Gln Gly Thr Gln Val Glu Ile Lys
        115                 120                 125

<210> SEQ ID NO 48
<211> LENGTH: 139
<212> TYPE: PRT
<213> ORGANISM: Artificial Sequence
<220> FEATURE:
<223> OTHER INFORMATION: Antibody 3 heavy chain variable region

<400> SEQUENCE: 48

Met Asp Trp Thr Trp Arg Phe Leu Phe Val Val Ala Ala Ala Thr Gly
```

-continued

```
                1               5                   10                  15
            Val Gln Ser Gln Val Gln Leu Val Gln Ser Gly Ala Glu Val Lys Lys
                            20                  25                  30
            Pro Gly Ser Ser Val Lys Val Ser Cys Lys Ala Ser Gly Gly Thr Leu
                            35                  40                  45
            Asn Asn Tyr Ala Ile Ser Trp Val Arg Gln Ala Pro Gly Gln Gly Leu
                        50                  55                  60
            Glu Trp Met Gly Gly Ile Ser Pro Ile Phe Gly Thr Leu Asn Tyr Ala
            65                  70                  75                  80
            Glu Arg Phe Gln Gly Arg Val Thr Ile Thr Ala Asp Val Phe Thr Asn
                                85                  90                  95
            Thr Val Tyr Met Glu Leu Ser Ser Leu Arg Ser Glu Asp Thr Ala Val
                            100                 105                 110
            Tyr Phe Cys Ala Arg Gly Cys Gly Tyr Asn Cys Tyr Tyr Phe Asp Gly
                        115                 120                 125
            Trp Gly Gln Gly Thr Leu Val Thr Val Ser Ser
                        130                 135
```

<210> SEQ ID NO 49
<211> LENGTH: 128
<212> TYPE: PRT
<213> ORGANISM: Artificial Sequence
<220> FEATURE:
<223> OTHER INFORMATION: Antibody 4 light chain variable region

<400> SEQUENCE: 49

```
            Met Glu Thr Pro Ala Gln Leu Leu Phe Leu Leu Leu Leu Trp Leu Pro
            1               5                   10                  15
            Asp Thr Thr Gly Glu Thr Val Leu Thr Gln Ser Pro Gly Thr Leu Ser
                            20                  25                  30
            Leu Ser Pro Gly Glu Arg Ala Thr Leu Ser Cys Arg Ala Ser Gln Ser
                        35                  40                  45
            Val Ser Ile Ser Tyr Leu Ala Trp Tyr Gln Arg Lys Pro Gly Gln Ala
                    50                  55                  60
            Pro Arg Leu Leu Ile Tyr Gly Ala Ser Arg Arg Ala Thr Gly Ile Pro
            65                  70                  75                  80
            Asp Arg Phe Ser Gly Ser Gly Ser Gly Thr Asp Phe Thr Leu Thr Ile
                            85                  90                  95
            Ser Arg Leu Glu Pro Glu Asp Phe Ala Val Tyr Tyr Cys Gln Gln Tyr
                        100                 105                 110
            Gly Ser Ser Pro Tyr Thr Phe Gly Gln Gly Thr Lys Leu Glu Ile Lys
                    115                 120                 125
```

<210> SEQ ID NO 50
<211> LENGTH: 146
<212> TYPE: PRT
<213> ORGANISM: Artificial Sequence
<220> FEATURE:
<223> OTHER INFORMATION: Antibody 4 heavy chain variable region

<400> SEQUENCE: 50

```
            Met Glu Phe Gly Leu Ser Trp Val Phe Leu Val Ala Leu Leu Arg Gly
            1               5                   10                  15
            Val Gln Cys Gln Val Gln Leu Val Glu Ser Gly Gly Gly Val Val Gln
                            20                  25                  30
            Pro Gly Arg Ser Leu Arg Leu Ser Cys Ala Ala Ser Gly Phe Thr Phe
                        35                  40                  45
```

-continued

Ser Arg Phe Gly Ile His Trp Val Arg Gln Ala Pro Gly Lys Gly Leu
    50                  55                  60

Glu Trp Met Ala Val Ile Trp Tyr Asp Gly Ser Asn Lys Phe Tyr Ala
65                  70                  75                  80

Asp Ser Val Lys Gly Arg Phe Thr Ile Ser Arg Asp Asn Ser Lys Asn
                85                  90                  95

Thr Val Tyr Leu Gln Met Asn Ser Leu Arg Ala Glu Asp Thr Ala Val
            100                 105                 110

Tyr Tyr Cys Ala Lys Asp Ser Arg Gly Tyr Cys Ser Ser Ile Ile Cys
        115                 120                 125

Phe Glu Gly Gly Leu Asp Asn Trp Gly Gln Gly Thr Leu Val Thr Val
    130                 135                 140

Ser Ser
145

<210> SEQ ID NO 51
<211> LENGTH: 108
<212> TYPE: PRT
<213> ORGANISM: Artificial Sequence
<220> FEATURE:
<223> OTHER INFORMATION: Antibody 5 light chain variable region

<400> SEQUENCE: 51

Glu Ile Val Leu Thr Gln Ser Pro Gly Thr Leu Ser Val Ser Pro Gly
1               5                   10                  15

Glu Arg Ala Thr Leu Ser Cys Arg Ala Ser Arg Arg Val Gly Ser Thr
            20                  25                  30

Tyr Leu Ala Trp Tyr Gln Gln Lys Pro Gly Gln Ala Pro Arg Arg Leu
        35                  40                  45

Ile Tyr Gly Ala Ser Ser Arg Ala Ala Gly Ile Pro Asp Arg Phe Ser
    50                  55                  60

Gly Thr Gly Ser Gly Thr Asp Phe Thr Leu Thr Ile Ser Arg Val Asp
65                  70                  75                  80

Pro Glu Asp Phe Ala Val Tyr Tyr Cys Gln Gln Tyr Ala Ala Ser Pro
                85                  90                  95

Trp Thr Phe Gly Gln Gly Thr Val Glu Ile Lys
            100                 105

<210> SEQ ID NO 52
<211> LENGTH: 126
<212> TYPE: PRT
<213> ORGANISM: Artificial Sequence
<220> FEATURE:
<223> OTHER INFORMATION: Antibody 5 heavy chain variable region

<400> SEQUENCE: 52

Gln Val Gln Leu Val Gln Ser Gly Gly Glu Leu Lys Lys Pro Gly Ala
1               5                   10                  15

Ser Val Arg Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Val
        35                  40                  45

Gly Trp Ile Ser Ala Tyr Thr Gly Asn Thr Asp Tyr Ala Gln Lys Val
    50                  55                  60

Gln Gly Arg Val Thr Met Thr Thr Asp Thr Ser Thr Ser Thr Ala Tyr
65                  70                  75                  80

Met Glu Leu Arg Ser Leu Thr Ser Asp Asp Thr Ala Val Tyr Tyr Cys
                85                  90                  95

-continued

Ala Arg Asp Lys Val Gln Gly Arg Val Glu Ala Gly Ser Gly Gly Arg
            100                 105                 110

His Asp Tyr Trp Gly Gln Gly Thr Leu Val Thr Val Ser Ser
            115                 120                 125

<210> SEQ ID NO 53
<211> LENGTH: 108
<212> TYPE: PRT
<213> ORGANISM: Artificial Sequence
<220> FEATURE:
<223> OTHER INFORMATION: Antibody 6 light chain variable region

<400> SEQUENCE: 53

Glu Val Val Leu Thr Gln Ser Pro Gly Thr Leu Thr Leu Pro Pro Gly
1               5                   10                  15

Asp Arg Ala Thr Leu Ser Cys Arg Ala Ser His Ser Val Gly Ser Thr
            20                  25                  30

Tyr Ile Ala Trp Phe Gln Gln Lys Ser Gly Gln Ala Pro Arg Arg Leu
        35                  40                  45

Ile Tyr Gly Ala Ser Asn Arg Ala Thr Asp Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Ser Ala Val Tyr Tyr Cys Gln Gln Phe Val Ser Pro
                85                  90                  95

Trp Thr Phe Gly Gln Gly Thr Arg Val Glu Ile Lys
            100                 105

<210> SEQ ID NO 54
<211> LENGTH: 126
<212> TYPE: PRT
<213> ORGANISM: Artificial Sequence
<220> FEATURE:
<223> OTHER INFORMATION: Antibody 6 heavy chain variable region

<400> SEQUENCE: 54

Gln Val Gln Leu Val Gln Ser Gly Val Glu Val Lys Lys Pro Gly Ala
1               5                   10                  15

Ser Val Lys Val Ser Cys Lys Thr Ser Gly Tyr Pro Phe Ser Thr Tyr
            20                  25                  30

Gly Val Ser Trp Val Arg Gln Ala Pro Gly Gln Gly Leu Glu Trp Val
        35                  40                  45

Gly Trp Ile Ser Gly Tyr Thr Gly Ile Thr Asp Tyr Ala Gln Lys Ser
    50                  55                  60

Gln Gly Arg Val Thr Leu Thr Thr Asp Ala Ser Thr Ala Thr Ala Phe
65                  70                  75                  80

Leu Glu Leu Arg Ser Leu Arg Pro Asp Asp Thr Ala Thr Tyr Phe Cys
                85                  90                  95

Ala Arg Asp Lys Val Gln Gly Arg Val Glu Ala Gly Ser Gly Gly Arg
            100                 105                 110

His Asp Tyr Trp Gly Gln Gly Thr Leu Val Ile Val Ser Ser
            115                 120                 125

<210> SEQ ID NO 55
<211> LENGTH: 108
<212> TYPE: PRT
<213> ORGANISM: Artificial Sequence
<220> FEATURE:
<223> OTHER INFORMATION: Antibody 7 light chain variable region

<400> SEQUENCE: 55

Glu Val Val Leu Thr Gln Ser Pro Gly Thr Leu Ala Leu Pro Pro Gly
1               5                   10                  15

Glu Arg Ala Thr Leu Ser Cys Arg Ala Ser His Ser Ile Gly Ser Thr
            20                  25                  30

Tyr Ile Ala Trp Tyr Gln Gln Lys Ser Gly Gln Ala Pro Arg Arg Leu
        35                  40                  45

Ile Tyr Gly Ala Ser Asn Arg Ala Ser Asp Ile Pro Asp Arg Phe Ser
50                  55                  60

Gly Ser Gly Ser Gly Thr Asp Phe Thr Leu Thr Ile Arg Arg Leu Glu
65                  70                  75                  80

Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys
            100                 105

<210> SEQ ID NO 56
<211> LENGTH: 126
<212> TYPE: PRT
<213> ORGANISM: Artificial Sequence
<220> FEATURE:
<223> OTHER INFORMATION: Antibody 7 heavy chain variable region

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Leu Glu Trp Val
        35                  40                  45

Gly Trp Ile Ser Gly Tyr Thr Gly Ile Thr Asp Tyr Ala Gln Lys Phe
50                  55                  60

Gln Gly Arg Val Thr Leu Thr Thr Asp Ala Thr Thr Ala Thr Ala Phe
65                  70                  75                  80

Leu Glu Leu Arg Ser Leu Arg Pro Asp Asp Thr Ala Thr Tyr Phe Cys
                85                  90                  95

Ala Arg Asp Lys Val Gln Gly Arg Val Glu Val Gly Ser Gly Gly Arg
            100                 105                 110

His Asp Tyr Trp Gly Gln Gly Thr Leu Val Ile Val Ser Ser
        115                 120                 125

<210> SEQ ID NO 57
<211> LENGTH: 234
<212> TYPE: PRT
<213> ORGANISM: Artificial Sequence
<220> FEATURE:
<223> OTHER INFORMATION: Antibody 1 light chain

<400> SEQUENCE: 57

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Ile Trp Asn Asn Leu Ala Trp Tyr Gln Gln Lys Pro Gly Gln Ala Pro
50                  55                  60

```
Arg Leu Leu Ile Ser Gly Ala Ser Thr Gly Ala Thr Gly Val Pro Ser
 65                  70                  75                  80

Arg Phe Arg Gly Ser Gly Ser Arg Thr Glu Phe Thr Leu Thr Ile Ser
             85                  90                  95

Ser Leu Gln Ser Glu Asp Phe Ala Ile Tyr Phe Cys Gln Gln Tyr Asn
            100                 105                 110

Ser Trp Pro Arg Thr Phe Gly Pro Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 58
<211> LENGTH: 472
<212> TYPE: PRT
<213> ORGANISM: Artificial Sequence
<220> FEATURE:
<223> OTHER INFORMATION: Antibody 1 heavy chain

<400> SEQUENCE: 58

Met Asp Trp Thr Trp Arg Phe Leu Phe Val Val Ala Ala Ala Thr Gly
  1               5                  10                  15

Val Gln Cys Gln Val Gln Leu Val Gln Ser Gly Ala Glu Val Lys Met
             20                  25                  30

Pro Gly Ser Ser Val Lys Val Ser Cys Lys Thr Ser Gly Val Phe Phe
             35                  40                  45

Ser Ser His Ala Ile Ser Trp Val Arg Gln Ala Pro Gly Gln Gly Leu
         50                  55                  60

Glu Trp Met Gly Gly Ile Ser Pro Met Phe Gly Thr Thr His Tyr Ala
 65                  70                  75                  80

Gln Lys Phe Gln Gly Arg Val Thr Ile Thr Ala Asp Gln Ser Thr Thr
             85                  90                  95

Thr Ala Tyr Met Glu Leu Thr Ser Leu Thr Ser Glu Asp Thr Ala Val
            100                 105                 110

Tyr Tyr Cys Ala Arg Asp Gly Ala Gly Ser Tyr Tyr Pro Leu Asn Trp
            115                 120                 125

Phe Asp Pro Trp Gly Gln Gly Thr Leu Val Thr Val Ser Ser Ala Ser
            130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
            180                 185                 190
```

His Thr Phe Pro Ala Val Leu Gln Ser Ser Gly Leu Tyr Ser Leu Ser
            195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Arg Glu Val Thr Cys Val Val
            275                 280                 285

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Gly Leu His Asn His Tyr Thr Gln Lys
            450                 455                 460

Ser Leu Ser Leu Phe Pro Gly Lys
465                 470

<210> SEQ ID NO 59
<211> LENGTH: 215
<212> TYPE: PRT
<213> ORGANISM: Artificial Sequence
<220> FEATURE:
<223> OTHER INFORMATION: Antibody 2 light chain

<400> SEQUENCE: 59

Glu Val Val Leu Thr Gln Ser Pro Gly Thr Leu Ala Leu Pro Pro Gly
1               5                   10                  15

Glu Arg Ala Thr Leu Ser Cys Arg Ala Ser His Arg Val Gly Ser Thr
            20                  25                  30

Tyr Ile Ala Trp Tyr Gln Gln Lys Ser Gly Gln Ala Pro Arg Arg Leu
        35                  40                  45

Ile Tyr Gly Ala Ser Asn Arg Ala Thr Asp Ile Pro Asp Arg Phe Ser
    50                  55                  60

Gly Ser Gly Ser Gly Thr Asp Phe Thr Leu Thr Ile Arg Arg Leu Glu
65                  70                  75                  80

```
Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 60
<211> LENGTH: 456
<212> TYPE: PRT
<213> ORGANISM: Artificial Sequence
<220> FEATURE:
<223> OTHER INFORMATION: Antibody 2 heavy chain

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
                20                  25                  30

Gly Val Ser Trp Val Arg Gln Ala Pro Gly Gln Gly Pro Glu Trp Val
            35                  40                  45

Gly Trp Ile Ser Ala Tyr Thr Gly Ile Thr Asp Tyr Ala Gln Lys Phe
    50                  55                  60

Gln Gly Arg Val Thr Leu Thr Thr Asp Ala Thr Ala Thr Ala Phe
65                  70                  75                  80

Leu Asp Leu Arg Ser Leu Arg Pro Asp Asp Thr Ala Thr Tyr Phe Cys
                85                  90                  95

Ala Arg Asp Lys Val Gln Gly Arg Val Glu Val Gly Ser Gly Gly Arg
            100                 105                 110

His Asp Tyr Trp Gly Gln Gly Thr Leu Val Ile Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220
```

```
Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Asp Glu Leu Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Gly Leu His Asn His Tyr Thr Gln Lys
    435                 440                 445

Ser Leu Ser Leu Ser Pro Gly Lys
    450                 455

<210> SEQ ID NO 61
<211> LENGTH: 235
<212> TYPE: PRT
<213> ORGANISM: Artificial Sequence
<220> FEATURE:
<223> OTHER INFORMATION: Antibody 3 light chain

<400> SEQUENCE: 61

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Leu Ser Ser Ser Leu Val Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
            85                  90                  95

Ser Arg Leu Glu Pro Glu Asp Phe Ala Val Tyr Tyr Cys Gln Gln Tyr
        100                 105                 110

Gly Asn Ser Pro Tyr Thr Phe Gly Gln Gly Thr Gln Val Glu Ile Lys
    115                 120                 125
```

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 62
<211> LENGTH: 469
<212> TYPE: PRT
<213> ORGANISM: Artificial Sequence
<220> FEATURE:
<223> OTHER INFORMATION: Antibody 3 heavy chain

<400> SEQUENCE: 62

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Leu
        35                  40                  45

Asn Asn Tyr Ala Ile Ser Trp Val Arg Gln Ala Pro Gly Gln Gly Leu
    50                  55                  60

Glu Trp Met Gly Gly Ile Ser Pro Ile Phe Gly Thr Leu Asn Tyr Ala
65                  70                  75                  80

Glu Arg Phe Gln Gly Arg Val Thr Ile Thr Ala Asp Val Phe Thr Asn
                85                  90                  95

Thr Val Tyr Met Glu Leu Ser Ser Leu Arg Ser Glu Asp Thr Ala Val
            100                 105                 110

Tyr Phe Cys Ala Arg Gly Cys Gly Tyr Asn Cys Tyr Tyr Phe Asp Gly
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Gly Leu His Asn Pro Tyr Thr Gln Lys Ser Leu Ser
450                 455                 460

Leu Phe Pro Gly Lys
465

<210> SEQ ID NO 63
<211> LENGTH: 235
<212> TYPE: PRT
<213> ORGANISM: Artificial Sequence
<220> FEATURE:
<223> OTHER INFORMATION: Antibody 4 light chain

<400> SEQUENCE: 63

Met Glu Thr Pro Ala Gln Leu Leu Phe Leu Leu Leu Leu Trp Leu Pro
1               5                   10                  15

Asp Thr Thr Gly Glu Thr Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ile Ser Tyr Leu Ala Trp Tyr Gln Arg Lys Pro Gly Gln Ala
    50                  55                  60

Pro Arg Leu Leu Ile Tyr Gly Ala Ser Arg Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Tyr Thr Phe Gly Gln Gly Thr Lys Leu Glu Ile Lys
        115                 120                 125

Arg Thr Val Ala Ala Pro Ser Val Phe Ile Phe Pro Pro Ser Asp Glu
    130                 135                 140

```
Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 64
<211> LENGTH: 476
<212> TYPE: PRT
<213> ORGANISM: Artificial Sequence
<220> FEATURE:
<223> OTHER INFORMATION: Antibody 4 heavy chain

<400> SEQUENCE: 64

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Arg Phe Gly Ile His Trp Val Arg Gln Ala Pro Gly Lys Gly Leu
50                  55                  60

Glu Trp Met Ala Val Ile Trp Tyr Asp Gly Ser Asn Lys Phe Tyr Ala
65                  70                  75                  80

Asp Ser Val Lys Gly Arg Phe Thr Ile Ser Arg Asp Asn Ser Lys Asn
                85                  90                  95

Thr Val Tyr Leu Gln Met Asn Ser Leu Arg Ala Glu Asp Thr Ala Val
            100                 105                 110

Tyr Tyr Cys Ala Lys Asp Ser Arg Gly Tyr Cys Ser Ser Ile Ile Cys
        115                 120                 125

Phe Glu Gly Gly Leu Asp Asn Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270
```

Pro Pro Lys Pro Lys Asp Thr Leu Met Ile Ser Arg Thr Pro Glu Val
          275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
          340                 345                 350

Ser Asn Lys Ala Leu Pro Ala Pro Ile Glu Lys Thr Ile Ser Lys Ala
          355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Phe Leu Tyr Ser Lys Leu Thr Val Asp Lys Ser Arg Trp Gln Gln
          435                 440                 445

Gly Asn Val Phe Ser Cys Ser Val Met His Glu Gly Leu His Asn His
          450                 455                 460

Tyr Thr Gln Lys Ser Leu Ser Leu Phe Pro Gly Lys
465                 470                 475

<210> SEQ ID NO 65
<211> LENGTH: 215
<212> TYPE: PRT
<213> ORGANISM: Artificial Sequence
<220> FEATURE:
<223> OTHER INFORMATION: Antibody 5 light chain

<400> SEQUENCE: 65

Glu Ile Val Leu Thr Gln Ser Pro Gly Thr Leu Ser Val Ser Pro Gly
1               5                   10                  15

Glu Arg Ala Thr Leu Ser Cys Arg Ala Ser Arg Arg Val Gly Ser Thr
            20                  25                  30

Tyr Leu Ala Trp Tyr Gln Gln Lys Pro Gly Gln Ala Pro Arg Arg Leu
        35                  40                  45

Ile Tyr Gly Ala Ser Ser Arg Ala Ala Gly Ile Pro Asp Arg Phe Ser
    50                  55                  60

Gly Thr Gly Ser Gly Thr Asp Phe Thr Leu Thr Ile Ser Arg Val Asp
65                  70                  75                  80

Pro Glu Asp Phe Ala Val Tyr Tyr Cys Gln Gln Tyr Ala Ala Ser Pro
                85                  90                  95

Trp Thr Phe Gly Gln Gly Thr Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

```
Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 66
<211> LENGTH: 456
<212> TYPE: PRT
<213> ORGANISM: Artificial Sequence
<220> FEATURE:
<223> OTHER INFORMATION: Antibody 5 heavy chain
<220> FEATURE:
<221> NAME/KEY: misc_feature
<222> LOCATION: (219)..(219)
<223> OTHER INFORMATION: Xaa can be any naturally occurring amino acid

<400> SEQUENCE: 66

Gln Val Gln Leu Val Gln Ser Gly Gly Glu Leu Lys Lys Pro Gly Ala
1               5                   10                  15

Ser Val Arg Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Val
            35                  40                  45

Gly Trp Ile Ser Ala Tyr Thr Gly Asn Thr Asp Tyr Ala Gln Lys Val
        50                  55                  60

Gln Gly Arg Val Thr Met Thr Thr Asp Thr Ser Thr Ser Thr Ala Tyr
65                  70                  75                  80

Met Glu Leu Arg Ser Leu Thr Ser Asp Asp Thr Ala Val Tyr Tyr Cys
                85                  90                  95

Ala Arg Asp Lys Val Gln Gly Arg Val Glu Ala Gly Ser Gly Gly Arg
            100                 105                 110

His Asp Tyr Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Xaa Val Asp Lys Lys Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
```

```
            275                 280                 285
Asp Gly Val Glu Val His Asn Ala Lys Thr Lys Pro Arg Glu Glu Gln
290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Asp Glu Leu Thr
        355                 360                 365
Lys Asn Gln Val Ser Leu Thr Cys Leu Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Gly Leu His Asn His Tyr Thr Gln Lys
        435                 440                 445
Ser Leu Ser Leu Ser Pro Gly Lys
    450                 455

<210> SEQ ID NO 67
<211> LENGTH: 215
<212> TYPE: PRT
<213> ORGANISM: Artificial Sequence
<220> FEATURE:
<223> OTHER INFORMATION: Antibody 6 light chain

<400> SEQUENCE: 67

Glu Val Val Leu Thr Gln Ser Pro Gly Thr Leu Thr Leu Pro Pro Gly
1               5                   10                  15
Asp Arg Ala Thr Leu Ser Cys Arg Ala Ser His Ser Val Gly Ser Thr
            20                  25                  30
Tyr Ile Ala Trp Phe Gln Gln Lys Ser Gly Gln Ala Pro Arg Arg Leu
        35                  40                  45
Ile Tyr Gly Ala Ser Asn Arg Ala Thr Asp Ile Pro Asp Arg Phe Ser
    50                  55                  60
Gly Ser Gly Ser Gly Thr Asp Phe Thr Leu Thr Ile Arg Arg Leu Glu
65                  70                  75                  80
Pro Glu Asp Ser Ala Val Tyr Tyr Cys Gln Gln Phe Ser Val Ser Pro
                85                  90                  95
Trp Thr Phe Gly Gln Gly Thr Arg Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
```

```
                    180                 185                 190
Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 68
<211> LENGTH: 456
<212> TYPE: PRT
<213> ORGANISM: Artificial Sequence
<220> FEATURE:
<223> OTHER INFORMATION: Antibody 6 heavy chain

<400> SEQUENCE: 68

Gln Val Gln Leu Val Gln Ser Gly Val Glu Val Lys Lys Pro Gly Ala
1               5                   10                  15

Ser Val Lys Val Ser Cys Lys Thr Ser Gly Tyr Pro Phe Ser Thr Tyr
            20                  25                  30

Gly Val Ser Trp Val Arg Gln Ala Pro Gly Gln Gly Leu Glu Trp Val
        35                  40                  45

Gly Trp Ile Ser Gly Tyr Thr Gly Ile Thr Asp Tyr Ala Gln Lys Ser
    50                  55                  60

Gln Gly Arg Val Thr Leu Thr Thr Asp Ala Ser Thr Ala Thr Ala Phe
65                  70                  75                  80

Leu Glu Leu Arg Ser Leu Arg Pro Asp Asp Thr Ala Thr Tyr Phe Cys
                85                  90                  95

Ala Arg Asp Lys Val Gln Gly Arg Val Glu Ala Gly Ser Gly Gly Arg
            100                 105                 110

His Asp Tyr Trp Gly Gln Gly Thr Leu Val Ile Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
```

```
                   325                 330                 335
Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Gly Leu His Asn His Tyr Thr Gln Lys
                435                 440                 445

Ser Leu Ser Leu Ser Pro Gly Lys
                450                 455

<210> SEQ ID NO 69
<211> LENGTH: 215
<212> TYPE: PRT
<213> ORGANISM: Artificial Sequence
<220> FEATURE:
<223> OTHER INFORMATION: Antibody 7 light chain

<400> SEQUENCE: 69

Glu Val Val Leu Thr Gln Ser Pro Gly Thr Leu Ala Leu Pro Pro Gly
1               5                   10                  15

Glu Arg Ala Thr Leu Ser Cys Arg Ala Ser His Ser Ile Gly Ser Thr
                20                  25                  30

Tyr Ile Ala Trp Tyr Gln Gln Lys Ser Gly Gln Ala Pro Arg Arg Leu
            35                  40                  45

Ile Tyr Gly Ala Ser Asn Arg Ala Ser Asp Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215
```

<210> SEQ ID NO 70
<211> LENGTH: 456
<212> TYPE: PRT
<213> ORGANISM: Artificial Sequence
<220> FEATURE:
<223> OTHER INFORMATION: Antibody 7 heavy chain

<400> SEQUENCE: 70

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Leu Glu Trp Val
        35                  40                  45

Gly Trp Ile Ser Gly Tyr Thr Gly Ile Thr Asp Tyr Ala Gln Lys Phe
    50                  55                  60

Gln Gly Arg Val Thr Leu Thr Thr Asp Ala Thr Ala Thr Ala Phe
65                  70                  75                  80

Leu Glu Leu Arg Ser Leu Arg Pro Asp Asp Thr Ala Thr Tyr Phe Cys
                85                  90                  95

Ala Arg Asp Lys Val Gln Gly Arg Val Glu Val Gly Ser Gly Gly Arg
            100                 105                 110

His Asp Tyr Trp Gly Gln Gly Thr Leu Val Ile Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
```

```
                    370                 375                 380
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Gly Leu His Asn His Tyr Thr Gln Lys
            435                 440                 445

Ser Leu Ser Leu Ser Pro Gly Lys
    450                 455
```

<210> SEQ ID NO 71
<211> LENGTH: 33
<212> TYPE: DNA
<213> ORGANISM: Artificial Sequence
<220> FEATURE:
<223> OTHER INFORMATION: Antibody 1 light chain CDR1

<400> SEQUENCE: 71
agggccagtg agaatatttg gaacaacttg gcc                          33

<210> SEQ ID NO 72
<211> LENGTH: 21
<212> TYPE: DNA
<213> ORGANISM: Artificial Sequence
<220> FEATURE:
<223> OTHER INFORMATION: Antibody 1 light chain CDR2

<400> SEQUENCE: 72
ggtgcgtcca ccggggccac t                                       21

<210> SEQ ID NO 73
<211> LENGTH: 27
<212> TYPE: DNA
<213> ORGANISM: Artificial Sequence
<220> FEATURE:
<223> OTHER INFORMATION: Antibody 1 light chain CDR3

<400> SEQUENCE: 73
cagcagtata attcgtggcc tcggacg                                 27

<210> SEQ ID NO 74
<211> LENGTH: 15
<212> TYPE: DNA
<213> ORGANISM: Artificial Sequence
<220> FEATURE:
<223> OTHER INFORMATION: Antibody 1 heavy chain CDR1

<400> SEQUENCE: 74
agtcatgcta tcagt                                              15

<210> SEQ ID NO 75
<211> LENGTH: 51
<212> TYPE: DNA
<213> ORGANISM: Artificial Sequence
<220> FEATURE:
<223> OTHER INFORMATION: Antibody 1 heavy chain CDR2

<400> SEQUENCE: 75
gggatcagcc ctatgtttgg aacaacacac tacgcacaga gttccaggg c       51

<210> SEQ ID NO 76

```
<211> LENGTH: 42
<212> TYPE: DNA
<213> ORGANISM: Artificial Sequence
<220> FEATURE:
<223> OTHER INFORMATION: Antibody 1 heavy chain CDR3

<400> SEQUENCE: 76
gatggtgcgg ggagttatta tccactcaac tggttcgacc cc                              42

<210> SEQ ID NO 77
<211> LENGTH: 36
<212> TYPE: DNA
<213> ORGANISM: Artificial Sequence
<220> FEATURE:
<223> OTHER INFORMATION: Antibody 2 light chain CDR1

<400> SEQUENCE: 77
agggccagtc accgtgttgg cagcacctac atagcc                                    36

<210> SEQ ID NO 78
<211> LENGTH: 21
<212> TYPE: DNA
<213> ORGANISM: Artificial Sequence
<220> FEATURE:
<223> OTHER INFORMATION: Antibody 2 light chain CDR2

<400> SEQUENCE: 78
ggtgcatcca cagggccac t                                                     21

<210> SEQ ID NO 79
<211> LENGTH: 27
<212> TYPE: DNA
<213> ORGANISM: Artificial Sequence
<220> FEATURE:
<223> OTHER INFORMATION: Antibody 2 light chain CDR3

<400> SEQUENCE: 79
cagcagttta gtgtttcacc gtggacg                                              27

<210> SEQ ID NO 80
<211> LENGTH: 15
<212> TYPE: DNA
<213> ORGANISM: Artificial Sequence
<220> FEATURE:
<223> OTHER INFORMATION: Antibody 2 heavy chain CDR1

<400> SEQUENCE: 80
acttatggag tcagt                                                           15

<210> SEQ ID NO 81
<211> LENGTH: 51
<212> TYPE: DNA
<213> ORGANISM: Artificial Sequence
<220> FEATURE:
<223> OTHER INFORMATION: Antibody 2 heavy chain CDR2

<400> SEQUENCE: 81
tggatcagcg cttacactgg tatcacagac tacgcacaga gtttcaggg c                    51

<210> SEQ ID NO 82
<211> LENGTH: 51
<212> TYPE: DNA
<213> ORGANISM: Artificial Sequence
<220> FEATURE:
<223> OTHER INFORMATION: Antibody 2 heavy chain CDR3

<400> SEQUENCE: 82
```
gataaggtgc aggggcgcgt tgaagtggga tctgggggtc gtcatgacta c        51

<210> SEQ ID NO 83
<211> LENGTH: 36
<212> TYPE: DNA
<213> ORGANISM: Artificial Sequence
<220> FEATURE:
<223> OTHER INFORMATION: Antibody 3 light chain CDR1

<400> SEQUENCE: 83
agggccagtc agagtcttag cagcagctcc ttagtc        36

<210> SEQ ID NO 84
<211> LENGTH: 20
<212> TYPE: DNA
<213> ORGANISM: Artificial Sequence
<220> FEATURE:
<223> OTHER INFORMATION: Antibody 3 light chain CDR2

<400> SEQUENCE: 84
ggtgcatcca gcagggccac        20

<210> SEQ ID NO 85
<211> LENGTH: 27
<212> TYPE: DNA
<213> ORGANISM: Artificial Sequence
<220> FEATURE:
<223> OTHER INFORMATION: Antibody 3 light chain CDR3

<400> SEQUENCE: 85
cagcagtatg ggaactcacc gtacacg        27

<210> SEQ ID NO 86
<211> LENGTH: 18
<212> TYPE: DNA
<213> ORGANISM: Artificial Sequence
<220> FEATURE:
<223> OTHER INFORMATION: Antibody 3 heavy chain CDR1

<400> SEQUENCE: 86
aacaactatg ctatcagc        18

<210> SEQ ID NO 87
<211> LENGTH: 54
<212> TYPE: DNA
<213> ORGANISM: Artificial Sequence
<220> FEATURE:
<223> OTHER INFORMATION: Antibody 3 heavy chain CDR2

<400> SEQUENCE: 87
ggagggatca gccctatctt tgggacatta aactacgcag agaggttcca gggc        54

<210> SEQ ID NO 88
<211> LENGTH: 33
<212> TYPE: DNA
<213> ORGANISM: Artificial Sequence
<220> FEATURE:
<223> OTHER INFORMATION: Antibody 3 heavy chain CDR3

<400> SEQUENCE: 88
ggttgtggct acaattgtta ctactttgac ggg        33

<210> SEQ ID NO 89
<211> LENGTH: 36
<212> TYPE: DNA

```
<213> ORGANISM: Artificial Sequence
<220> FEATURE:
<223> OTHER INFORMATION: Antibody 4 light chain CDR1

<400> SEQUENCE: 89
agggccagtc agagtgttag catcagctac ttagcc                                    36

<210> SEQ ID NO 90
<211> LENGTH: 21
<212> TYPE: DNA
<213> ORGANISM: Artificial Sequence
<220> FEATURE:
<223> OTHER INFORMATION: Antibody 4 light chain CDR2

<400> SEQUENCE: 90
ggcgcatcca ggagggccac t                                                    21

<210> SEQ ID NO 91
<211> LENGTH: 27
<212> TYPE: DNA
<213> ORGANISM: Artificial Sequence
<220> FEATURE:
<223> OTHER INFORMATION: Antibody 4 light chain CDR3

<400> SEQUENCE: 91
cagcagtatg gtagctcacc gtacact                                              27

<210> SEQ ID NO 92
<211> LENGTH: 15
<212> TYPE: DNA
<213> ORGANISM: Artificial Sequence
<220> FEATURE:
<223> OTHER INFORMATION: Antibody 4 heavy chain CDR1

<400> SEQUENCE: 92
aggtttggca tccac                                                           15

<210> SEQ ID NO 93
<211> LENGTH: 51
<212> TYPE: DNA
<213> ORGANISM: Artificial Sequence
<220> FEATURE:
<223> OTHER INFORMATION: Antibody 4 heavy chain CDR2

<400> SEQUENCE: 93
gttatatggt acgatggaag taataaattc tatgcagact ccgtgaaggg c                   51

<210> SEQ ID NO 94
<211> LENGTH: 54
<212> TYPE: DNA
<213> ORGANISM: Artificial Sequence
<220> FEATURE:
<223> OTHER INFORMATION: Antibody 4 heavy chain CDR3

<400> SEQUENCE: 94
gattcccgcg gatattgtag tagtatcatt tgttttgagg ggggacttga caac                54

<210> SEQ ID NO 95
<211> LENGTH: 36
<212> TYPE: DNA
<213> ORGANISM: Artificial Sequence
<220> FEATURE:
<223> OTHER INFORMATION: Antibody 5 light chain CDR1

<400> SEQUENCE: 95
agggccagtc ggcgcgttgg cagcacctac ttagcc                                    36
```

<210> SEQ ID NO 96
<211> LENGTH: 21
<212> TYPE: DNA
<213> ORGANISM: Artificial Sequence
<220> FEATURE:
<223> OTHER INFORMATION: Antibody 5 light chain CDR2

<400> SEQUENCE: 96
ggtgcatcca gcagggccgc t                                             21

<210> SEQ ID NO 97
<211> LENGTH: 27
<212> TYPE: DNA
<213> ORGANISM: Artificial Sequence
<220> FEATURE:
<223> OTHER INFORMATION: Antibody 5 light chain CDR3

<400> SEQUENCE: 97
cagcagtatg ctgcctcacc gtggacg                                       27

<210> SEQ ID NO 98
<211> LENGTH: 15
<212> TYPE: DNA
<213> ORGANISM: Artificial Sequence
<220> FEATURE:
<223> OTHER INFORMATION: Antibody 5 heavy chain CDR1

<400> SEQUENCE: 98
acctatggca tcagc                                                    15

<210> SEQ ID NO 99
<211> LENGTH: 51
<212> TYPE: DNA
<213> ORGANISM: Artificial Sequence
<220> FEATURE:
<223> OTHER INFORMATION: Antibody 5 heavy chain CDR2

<400> SEQUENCE: 99
tggatcagcg cttatactgg aaatacagac tatgcacaga aggtccaggg c             51

<210> SEQ ID NO 100
<211> LENGTH: 51
<212> TYPE: DNA
<213> ORGANISM: Artificial Sequence
<220> FEATURE:
<223> OTHER INFORMATION: Antibody 5 heavy chain CDR3

<400> SEQUENCE: 100
gataaggtcc aggggcgcgt tgaagcggga agtgggggcc ggcatgacta c             51

<210> SEQ ID NO 101
<211> LENGTH: 36
<212> TYPE: DNA
<213> ORGANISM: Artificial Sequence
<220> FEATURE:
<223> OTHER INFORMATION: Antibody 6 light chain CDR1

<400> SEQUENCE: 101
agggccagtc acagtgttgg cagcacctac atagcc                             36

<210> SEQ ID NO 102
<211> LENGTH: 21
<212> TYPE: DNA
<213> ORGANISM: Artificial Sequence
<220> FEATURE:

```
<223> OTHER INFORMATION: Antibody 6 light chain CDR2

<400> SEQUENCE: 102
ggtgcatcca acagggccac t                                              21

<210> SEQ ID NO 103
<211> LENGTH: 27
<212> TYPE: DNA
<213> ORGANISM: Artificial Sequence
<220> FEATURE:
<223> OTHER INFORMATION: Antibody 6 light chain CDR3

<400> SEQUENCE: 103
cagcagttta gtgtttcacc gtggacg                                        27

<210> SEQ ID NO 104
<211> LENGTH: 15
<212> TYPE: DNA
<213> ORGANISM: Artificial Sequence
<220> FEATURE:
<223> OTHER INFORMATION: Antibody 6 heavy chain CDR1

<400> SEQUENCE: 104
acttatggag tcagc                                                     15

<210> SEQ ID NO 105
<211> LENGTH: 51
<212> TYPE: DNA
<213> ORGANISM: Artificial Sequence
<220> FEATURE:
<223> OTHER INFORMATION: Antibody 6 heavy chain CDR2

<400> SEQUENCE: 105
tggatcagcg gttatactgg tatcacagac tacgcacaga agtctcaggg c              51

<210> SEQ ID NO 106
<211> LENGTH: 51
<212> TYPE: DNA
<213> ORGANISM: Artificial Sequence
<220> FEATURE:
<223> OTHER INFORMATION: Antibody 6 heavy chain CDR3

<400> SEQUENCE: 106
gacaaagtgc aggggcgcgt tgaagcggga tctgggggtc gtcacgacta c              51

<210> SEQ ID NO 107
<211> LENGTH: 36
<212> TYPE: DNA
<213> ORGANISM: Artificial Sequence
<220> FEATURE:
<223> OTHER INFORMATION: Antibody 7 light chain CDR1

<400> SEQUENCE: 107
agggccagtc acagtattgg cagcacctac atagcc                              36

<210> SEQ ID NO 108
<211> LENGTH: 21
<212> TYPE: DNA
<213> ORGANISM: Artificial Sequence
<220> FEATURE:
<223> OTHER INFORMATION: Antibody 7 light chain CDR2

<400> SEQUENCE: 108
ggtgcatcca acagggcctc t                                              21
```

-continued

<210> SEQ ID NO 109
<211> LENGTH: 27
<212> TYPE: DNA
<213> ORGANISM: Artificial Sequence
<220> FEATURE:
<223> OTHER INFORMATION: Antibody 7 light chain CDR3

<400> SEQUENCE: 109
cagcagttta gtgtttcacc gtggacg                                27

<210> SEQ ID NO 110
<211> LENGTH: 15
<212> TYPE: DNA
<213> ORGANISM: Artificial Sequence
<220> FEATURE:
<223> OTHER INFORMATION: Antibody 7 heavy chain CDR1

<400> SEQUENCE: 110
acttatggag tcagc                                             15

<210> SEQ ID NO 111
<211> LENGTH: 51
<212> TYPE: DNA
<213> ORGANISM: Artificial Sequence
<220> FEATURE:
<223> OTHER INFORMATION: Antibody 7 heavy chain CDR2

<400> SEQUENCE: 111
tggatcagcg gttacactgg tatcacagac tacgcacaga gtttcaggg c       51

<210> SEQ ID NO 112
<211> LENGTH: 51
<212> TYPE: DNA
<213> ORGANISM: Artificial Sequence
<220> FEATURE:
<223> OTHER INFORMATION: Antibody 7 heavy chain CDR3

<400> SEQUENCE: 112
gataaggtgc aggggcgcgt tgaagtggga tctggggtc gtcatgacta c       51

<210> SEQ ID NO 113
<211> LENGTH: 381
<212> TYPE: DNA
<213> ORGANISM: Artificial Sequence
<220> FEATURE:
<223> OTHER INFORMATION: Antibody 1 light chain variable region

<400> SEQUENCE: 113
atggaagccc cagctcagct tctcttcctc ctgctactct ggctcccaga taccaccgga       60
gaaattgtgt tgacacagtc tccagccacc ttgtctttgt ctccagggga aagagccacc      120
ctctcctgca gggccagtga gaatatttgg aacaacttgg cctggtacca gcaaaaacct      180
ggccaggctc ccaggctcct catctctggt gcgtccaccg gggccactgg tgtcccaagt      240
aggtttagag gcagcgggtc taggacagaa ttcactctca ccatcagcag cctgcagtct      300
gaagattttg caatttattt ctgtcagcag tataattcgt ggcctcggac gttcggccca      360
gggaccaagg tggagatcaa a                                                381

<210> SEQ ID NO 114
<211> LENGTH: 426
<212> TYPE: DNA
<213> ORGANISM: Artificial Sequence
<220> FEATURE:
<223> OTHER INFORMATION: Antibody 1 heavy chain variable region

```
<400> SEQUENCE: 114
atggactgga cctggaggtt cctctttgtg gtggcagcag ctacaggtgt ccagtgccag    60
gtgcagctgg tgcagtctgg ggctgaggtg aagatgcctg ggtcctcggt gaaggtctcc   120
tgcaagactt ctggagtctt cttcagcagt catgctatca gttgggtgcg acaggcccct   180
ggacaagggc ttgagtggat gggagggatc agccctatgt ttggaacaac acactacgca   240
cagaagttcc agggcagagt cacgattacc gcggaccaat ccacgaccac agcctacatg   300
gagttgacca gtcttacatc tgaggacacg gccgtatatt actgtgcgcg tgatggtgcg   360
gggagttatt atccactcaa ctggttcgac ccctggggcc agggaaccct ggtcaccgtc   420
tcctca                                                              426

<210> SEQ ID NO 115
<211> LENGTH: 324
<212> TYPE: DNA
<213> ORGANISM: Artificial Sequence
<220> FEATURE:
<223> OTHER INFORMATION: Antibody 2 light chain variable region

<400> SEQUENCE: 115
gaagttgtgt tgacacagtc tcccggcacc ctggctttgc ctccagggga aagagccacc    60
ctctcctgca gggccagtca ccgtgttggc agcacctaca gcctggtat cagcagaag   120 tctggccagg ctcccaggcg cctcatctat ggtgcatcca caggggccac tgacatccca   180
gacaggttca gtggcagtgg gtccgggaca gacttcactc tcaccatcag gagactggag   240
cctgaagatt ctgcagtgta ttactgtcag cagtttagtg tttcaccgtg gacgttcggc   300
caagggacca gggtggaaat caag                                          324

<210> SEQ ID NO 116
<211> LENGTH: 378
<212> TYPE: DNA
<213> ORGANISM: Artificial Sequence
<220> FEATURE:
<223> OTHER INFORMATION: Antibody 2 heavy chain variable region

<400> SEQUENCE: 116
caggttcagc tggtgcagtc tggagctgag gtgaagaagc ctggggcctc agtgaaggtc    60
tcctgcaaga cttctggtta ttccttttcc acttatggag tcagttgggt ccgacaggcc   120
cccggacaag ggcctgagtg ggtgggatgg atcagcgctt acactggtat cacagactac   180
gcacagaagt ttcagggcag agtcactctg accacagacg caaccacggc caccgccttc   240
ctggacctga ggagtctgag acctgacgac acggccacgt atttctgtgc gagagataag   300
gtgcaggggc gcgttgaagt gggatctggg ggtcgtcatg actactgggg acagggaacc   360
ctggtcatcg tctcctca                                                 378

<210> SEQ ID NO 117
<211> LENGTH: 384
<212> TYPE: DNA
<213> ORGANISM: Artificial Sequence
<220> FEATURE:
<223> OTHER INFORMATION: Antibody 3 light chain variable region

<400> SEQUENCE: 117
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtcttagc agcagctcct tagtctggta ccagcagaaa   180
```

```
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cagtatggga actcaccgta cacgtttggc    360
caggggaccc aggttgagat caaa                                          384

<210> SEQ ID NO 118
<211> LENGTH: 417
<212> TYPE: DNA
<213> ORGANISM: Artificial Sequence
<220> FEATURE:
<223> OTHER INFORMATION: Antibody 3 heavy chain variable region

<400> SEQUENCE: 118
atggactgga cctggaggtt cctctttgtg gtggcagcag ctacaggtgt ccagtcccag     60
gtgcagctgg tgcagtctgg ggctgaggtg aagaagcctg gtcctcggt gaaggtctcc    120 tgcaaggctt ctggaggcac cctcaacaac tatgctatca gctgggtgcg acaggcccct    180
ggacaagggc ttgagtggat gggagggatc agccctatct ttgggacatt aaactacgca    240
gagaggttcc agggcagagt caccattacc gcggacgtat ttacgaacac agtctacatg    300
gagctgagca gcctgagatc tgaggacacg gccgtgtatt tctgtgcgag aggttgtggc    360
tacaattgtt actactttga cgggtggggc cagggaaccc tggtcaccgt ttcctca      417

<210> SEQ ID NO 119
<211> LENGTH: 384
<212> TYPE: DNA
<213> ORGANISM: Artificial Sequence
<220> FEATURE:
<223> OTHER INFORMATION: Antibody 4 light chain variable region

<400> SEQUENCE: 119
atggaaaccc cagcgcagct tctcttcctc ctgctactct ggctcccaga taccaccgga     60
gaaactgtgt tgacgcagtc tccaggcacc ctgtctttgt ctccagggga agagccacc    120 ctctcctgca gggccagtca gagtgttagc atcagctact tagcctggta ccagcggaaa    180
cctggccagg ctcccaggct cctcatctat ggcgcatcca gagggccac tggcatccca    240 gacaggttca gtggcagtgg gtctgggaca gacttcactc tcaccatcag cagactggag    300
cctgaagatt ttgcagtata ttactgtcag cagtatggta gctcaccgta cacttttggc    360
caggggacca agctggagat caaa                                          384

<210> SEQ ID NO 120
<211> LENGTH: 438
<212> TYPE: DNA
<213> ORGANISM: Artificial Sequence
<220> FEATURE:
<223> OTHER INFORMATION: Antibody 4 heavy chain variable region

<400> SEQUENCE: 120
atggagtttg ggctgagctg gttttcctc gttgctcttt taagaggtgt ccagtgtcag     60
gtgcagctgg tggagtctgg gggaggcgtg gtccagcctg gaggtccct gagactctcc    120 tgtgcagcgt ctggattcac cttcagtagg tttggcatcc actgggtccg ccaggctcca    180
ggcaaggggc tggagtggat ggcagttata tggtacgatg aagtaataa attctatgca    240 gactccgtga aggccgatt caccatctcc agagacaatt ccaagaacac ggtttatctg    300
caaatgaaca gcctcagagc cgaggacacg gctgtctatt actgtgcgaa agattcccgc    360
```

```
ggatattgta gtagtatcat ttgttttgag gggggacttg acaactgggg ccagggaacc    420
ctggtcaccg tctcctca                                                  438

<210> SEQ ID NO 121
<211> LENGTH: 324
<212> TYPE: DNA
<213> ORGANISM: Artificial Sequence
<220> FEATURE:
<223> OTHER INFORMATION: Antibody 5 light chain variable region

<400> SEQUENCE: 121
gagattgtgt tgactcagtc tccaggcacc ctgtctgtgt ctccagggga aagagccacc    60
ctctcctgca gggccagtcg cgcgttggc agcacctact tagcctggta ccagcagaaa    120
cctggccagg ctcccaggcg cctcatctat ggtgcatcca gcaggccgc tggcatccca    180 gacaggttca gtggcactgg gtctgggaca gacttcactc tcaccatcag cagggtggac    240
cctgaagatt ttgcggtata ttactgtcag cagtatgctg cctcaccgtg gacgttcggc    300
caagggacca cggtggagat caaa                                           324

<210> SEQ ID NO 122
<211> LENGTH: 378
<212> TYPE: DNA
<213> ORGANISM: Artificial Sequence
<220> FEATURE:
<223> OTHER INFORMATION: Antibody 5 heavy chain variable region

<400> SEQUENCE: 122
caggttcagc tggtgcagtc tggaggtgag ctgaagaagc ctggggcctc agtgagggtc    60
tcctgtaagg cttctggcta cacctttacc acctatggca tcagctgggt gcgacaggcc    120
cctggacaag gccttgagtg gtgggatgg atcagcgctt atactggaaa tacagactat    180
gcacagaagg tccagggcag agtaaccatg accacggaca tccacgag cacagcctac     240 atggagctga ggagcctcac atctgacgac acggccgtct attactgtgc gagagataag    300 gtccagggc gcgttgaagc gggaagtggg ggccggcatg actactgggg ccagggaacc     360
ctggtcaccg tctcctca                                                   378

<210> SEQ ID NO 123
<211> LENGTH: 324
<212> TYPE: DNA
<213> ORGANISM: Artificial Sequence
<220> FEATURE:
<223> OTHER INFORMATION: Antibody 6 light chain variable region

<400> SEQUENCE: 123
gaagttgtgt tgacgcagtc tcccggcacc ctgactttgc ctccagggga cagagccacc    60
ctctcctgca gggccagtca cagtgttggc agcacctaca tagcctggtt tcagcagaag    120
tctggccagg ctcccaggcg cctcatctat ggtgcatcca acagggccac tgacatccca    180
gacaggttca gtggcagtgg gtccgggaca gacttcactc tcaccatcag gagactggag    240
cctgaagatt ctgcagtgta ctactgtcag cagtttagtg tttcaccgtg gacgttcggc    300
caagggacca gggtggaaat caag                                           324

<210> SEQ ID NO 124
<211> LENGTH: 378
<212> TYPE: DNA
<213> ORGANISM: Artificial Sequence
<220> FEATURE:
<223> OTHER INFORMATION: Antibody 6 heavy chain variable region
```

<400> SEQUENCE: 124

```
caggttcagc tggtccagtc tggagtagag gtgaagaagc tggggcctc agtgaaggtc      60
tcctgcaaga cttctggtta tccgttttcc acttatggag tcagctgggt ccgacaggcc    120
cctggacaag gcttgagtg gtgggatgg atcagcggtt atactggtat cacagactac     180
gcacagaagt ctcagggcag agtcactctg acgacagacg caagcacggc caccgccttc    240
ttggagctga ggagtctgag gcctgacgac acggccacct attttttgtgc gagagacaaa   300
gtgcaggggc gcgttgaagc gggatctggg ggtcgtcacg actactgggg acagggaacc    360
ctggtcatcg tctcctca                                                  378
```

<210> SEQ ID NO 125
<211> LENGTH: 324
<212> TYPE: DNA
<213> ORGANISM: Artificial Sequence
<220> FEATURE:
<223> OTHER INFORMATION: Antibody 7 light chain variable region

<400> SEQUENCE: 125

```
gaagttgtgt tgacgcagtc tcccggcacc ctggctttgc ctccagggga aagagccacc     60
ctctcctgca gggccagtca cagtattggc agcacctaca tagcctggta tcagcagaag   120
tctggccagg ctcccaggcg cctcatctat ggtgcatcca acagggcctc tgacatccca    180
gacaggttca gtggcagtgg gtccgggaca gacttcactc tcaccatcag gagactggag    240
cctgaagatt ctgcagtgta ttactgtcag cagtttagtg tttcaccgtg acgttcggc     300
caagggacca gggtggaaat caag                                           324
```

<210> SEQ ID NO 126
<211> LENGTH: 378
<212> TYPE: DNA
<213> ORGANISM: Artificial Sequence
<220> FEATURE:
<223> OTHER INFORMATION: Antibody 7 heavy chain variable region

<400> SEQUENCE: 126

```
caggttcagc tggtgcagtc tggagctgag gtgaagaagc tggggcctc agtgaaggtc      60
tcctgcaaga cttctggtta ttcctttttcc acttatggag tcagctgggt ccgacaggcc   120
cctggacaag gcttgagtg gtgggatgg atcagcggtt acactggtat cacagactac      180
gcacagaagt ttcagggcag agtcactctg accacagacg caaccacggc caccgccttc    240
ctggagctga ggagtctgag acctgacgac acggccacct atttctgtgc gagagataag    300
gtgcaggggc gcgttgaagt gggatctggg ggtcgtcatg actactgggg acagggaacc    360
ctggtcatcg tctcctca                                                  378
```

<210> SEQ ID NO 127
<211> LENGTH: 705
<212> TYPE: DNA
<213> ORGANISM: Artificial Sequence
<220> FEATURE:
<223> OTHER INFORMATION: Antibody 1 light chain

<400> SEQUENCE: 127

```
atggaagccc cagctcagct tctcttcctc ctgctactct ggctcccaga taccaccgga     60
gaaattgtgt tgacacagtc tccagccacc ttgtctttgt ctccagggga aagagccacc   120
ctctcctgca gggccagtga gaatatttgg aacaacttgg cctggtacca gcaaaaacct    180
```

| | |
|---|---|
| ggccaggctc ccaggctcct catctctggt gcgtccaccg ggccactggg tgtcccaagt | 240 |
| aggtttagag gcagcgggtc taggacagaa ttcactctca ccatcagcag cctgcagtct | 300 |
| gaagattttg caatttattt ctgtcagcag tataattcgt ggcctcggac gttcggccca | 360 |
| gggaccaagg tggagatcaa acgaactgtg gctgcaccat ctgtcttcat cttcccgcca | 420 |
| tctgatgagc agttgaaatc tggaactgcc tctgttgtgt gcctgctgaa taacttctat | 480 |
| cccagagagg ccaaagtaca gtggaaggtg gataacgccc tccaatcggg taactcccag | 540 |
| gagagtgtca cagagcagga cagcaaggac agcacctaca gcctcagcag caccctgacg | 600 |
| ctgagcaaag cagactacga gaaacacaaa gtctacgcct gcgaagtcac ccatcagggc | 660 |
| ctgagctcgc ccgtcacaaa gagcttcaac aggggagagt gttag | 705 |

<210> SEQ ID NO 128
<211> LENGTH: 1419
<212> TYPE: DNA
<213> ORGANISM: Artificial Sequence
<220> FEATURE:
<223> OTHER INFORMATION: Antibody 1 heavy chain

<400> SEQUENCE: 128

| | |
|---|---|
| atggactgga cctggaggtt cctctttgtg gtggcagcag ctacaggtgt ccagtgccag | 60 |
| gtgcagctgg tgcagtctgg ggctgaggtg aagatgcctg gtcctcggt gaaggtctcc | 120 |
| tgcaagactt ctggagtctt cttcagcagt catgctatca gttgggtgcg acaggcccct | 180 |
| ggacaagggc ttgagtggat gggagggatc agccctatgt ttggaacaac acactacgca | 240 |
| cagaagttcc agggcagagt cacgattacc gcggaccaat ccacgaccac agcctacatg | 300 |
| gagttgacca gtcttacatc tgaggacacg gccgtatatt actgtgcgcg tgatggtgcg | 360 |
| gggagttatt atccactcaa ctggttcgac cctgggggcc agggaaccct ggtcaccgtc | 420 |
| tcctcagcct ccaccaaggg cccatcggtc ttccccctgg cacctcctc caagagcacc | 480 |
| tctgggggca gcggccct gggctgcctg gtcaaggact acttccccga accggtgacg | 540 |
| gtgtcgtgga actcaggcgc cctgaccagc ggcgtgcaca ccttcccggc tgtcctacag | 600 |
| tcctcaggac tctactccct cagcagcgtg gtgaccgtgc cctccagcag cttgggcacc | 660 |
| cagacctaca tctgcaacgt gaatcacaag cccagcaaca ccaaggtgga caagagagtt | 720 |
| gagcccaaat cttgtgacaa aactcacaca tgcccaccgt gcccagcacc tgaactcctg | 780 |
| gggggaccgt cagtcttcct cttccccca aaacccaagg acaccctcat gatctcccgg | 840 |
| acccgtgagg tcacatgcgt ggtggtggac gtgagccacg aagaccctga ggtcaagttc | 900 |
| aactggtacg tggacggcgt ggaggtgcat aatgccaaga caaagccgcg ggaggagcag | 960 |
| tacaacagca cgtaccgtgt ggtcagcgtc ctcaccgtcc tgcaccagga ctggctgaat | 1020 |
| ggcaaggagt acaagtgcaa ggtctccaac aaagccctcc cagccccat cgagaaaacc | 1080 |
| atctccaaag ccaaagggca gccccgagaa ccacaggtgt acaccctgcc cccatcccgg | 1140 |
| gatgagctga ccaagaacca ggtcagcctg acctgcctgg tcaaaggctt ttatcccagc | 1200 |
| gacatcgccg tggagtggga gagcaatggg cagccggaga caactacaa gaccacgcct | 1260 |
| cccgtgctgg actccgacgg ctccttttc ctttacagca agctcaccgt ggacaagagc | 1320 |
| aggtggcagc aggggaacgt ctttttcatgc tccgtgatgc atgagggttt gcacaaccac | 1380 |
| tacacgcaga agagcctctc cctgtttccg ggtaaatga | 1419 |

<210> SEQ ID NO 129
<211> LENGTH: 648

```
<212> TYPE: DNA
<213> ORGANISM: Artificial Sequence
<220> FEATURE:
<223> OTHER INFORMATION: Antibody 2 light chain

<400> SEQUENCE: 129
gaagttgtgt tgacacagtc tcccggcacc ctggctttgc ctccagggga aagagccacc     60
ctctcctgca gggccagtca ccgtgttggc agcacctaca tagcctggta tcagcagaag    120
tctggccagg ctcccaggcg cctcatctat ggtgcatcca cagggccac tgacatccca     180
gacaggttca gtggcagtgg gtccgggaca gacttcactc tcaccatcag gagactggag    240
cctgaagatt ctgcagtgta ttactgtcag cagtttagtg tttcaccgtg acgttcggc     300
caagggacca gggtggaaat caagcgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttag                 648

<210> SEQ ID NO 130
<211> LENGTH: 1371
<212> TYPE: DNA
<213> ORGANISM: Artificial Sequence
<220> FEATURE:
<223> OTHER INFORMATION: Antibody 2 heavy chain

<400> SEQUENCE: 130
caggttcagc tggtgcagtc tggagctgag gtgaagaagc ctggggcctc agtgaaggtc     60
tcctgcaaga cttctggtta ttccttttcc acttatggag tcagttgggt ccgacaggcc    120
cccggacaag ggcctgagtg ggtgggatgg atcagcgctt acactggtat cacagactac    180
gcacagaagt ttcagggcag agtcactctg accacagacg caaccacggc caccgccttc    240
ctggacctga ggagtctgag acctgacgac acggccacgt atttctgtgc gagagataag    300
gtgcaggggc gcgttgaagt gggatctggg ggtcgtcatg actactgggg acagggaacc    360
ctggtcatcg tctcctcagc ctccaccaag ggcccatcgg tcttcccct ggcaccctcc     420
tccaagagca cctctggggg cacagcggcc ctgggctgcc tggtcaagga ctacttcccc    480
gaaccggtga cggtgtcgtg gaactcaggc gccctgacca gcggcgtgca ccttcccg      540
gctgtcctac agtcctcagg actctactcc ctcagcagcg tggtgaccgt gcctccagc     600
agcttgggca cccagaccta catctgcaac gtgaatcaca agcccagcaa caccaaggtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtacaccctg   1080
cccccatccc gggatgagct gaccaagaac caggtcagcc tgacctgcct ggtcaaaggc   1140
ttctatccca gcgacatcgc cgtggagtgg gagagcaatg gcagccgga gaacaactac   1200
```

```
aagaccacgc ctcccgtgct ggactccgac ggctccttct tcctctacag caagctcacc    1260
gtggacaaga gcaggtggca gcaggggaac gtcttctcat gctccgtgat gcatgagggt    1320
ctgcacaacc actacacgca gaagagcctc tccctgtctc cgggtaaatg a             1371

<210> SEQ ID NO 131
<211> LENGTH: 708
<212> TYPE: DNA
<213> ORGANISM: Artificial Sequence
<220> FEATURE:
<223> OTHER INFORMATION: Antibody 3 light chain

<400> SEQUENCE: 131
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtcttagc agcagctcct tagtctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggga actcaccgta cacgtttggc     360
caggggaccc aggttgagat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactta cgagaaacac aaagtctacg cctgcgaagt cacccatcag     660
ggcctgagct cgcccgtcac aaagagcttc aacaggggag agtgttag                  708

<210> SEQ ID NO 132
<211> LENGTH: 1410
<212> TYPE: DNA
<213> ORGANISM: Artificial Sequence
<220> FEATURE:
<223> OTHER INFORMATION: Antibody 3 heavy chain

<400> SEQUENCE: 132
atggactgga cctggaggtt cctctttgtg gtggcagcag ctacaggtgt ccagtcccag      60
gtgcagctgg tgcagtctgg ggctgaggtg aagaagcctg gtcctcggt gaaggtctcc      120 tgcaaggctt ctggaggcac cctcaacaac tatgctatca gctgggtgcg acaggcccct     180
ggacaagggc ttgagtggat gggagggatc agccctatct ttgggacatt aaactacgca     240
gagaggttcc agggcagagt caccattacc gcggacgtat ttacgaacac agtctacatg     300
gagctgagca gcctgagatc tgaggacacg gccgtgtatt tctgtgcgag aggttgtggc     360
tacaattgtt actactttga cgggtggggc cagggaaccc tggtcaccgt ttcctcagcc     420
tccaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
```

```
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagccccca tcgagaaaac catctccaaa     1080 gccaagggc agccccgaga accacaggtg tacaccctgc ccccatcccg ggatgagctg      1140
accaagaacc aggtcagcct gacctgcctg gtcaaaggct tctatcccag cgacatcgcc     1200
gtggagtggg agagcaatgg gcagccggag aacaactaca agaccacgcc tcccgtgctg     1260
gactccgacg gctccttttt cctttacagc aagctcaccg tggacaagag caggtggcag     1320
caggggaacg ttttttcatg ctccgtgatg catgagggtt tgcacaaccc ctacacgcag     1380
aagagcctct ccctgtttcc gggtaaatga                                     1410
```

<210> SEQ ID NO 133
<211> LENGTH: 708
<212> TYPE: DNA
<213> ORGANISM: Artificial Sequence
<220> FEATURE:
<223> OTHER INFORMATION: Antibody 4 light chain

<400> SEQUENCE: 133

```
atggaaaccc cagcgcagct tctcttcctc ctgctactct ggctcccaga taccaccgga       60
gaaactgtgt tgacgcagtc tccaggcacc ctgtctttgt ctccagggga aagagccacc      120
ctctcctgca gggccagtca gagtgttagc atcagctact tagcctggta ccagcggaaa      180
cctggccagg ctcccaggct cctcatctat ggcgcatcca ggagggccac tggcatccca      240
gacaggttca gtggcagtgg gtctgggaca gacttcactc tcaccatcag cagactggag      300
cctgaagatt ttgcagtata ttactgtcag cagtatggta gctcaccgta cacttttggc      360
caggggacca agctggagat caaacgaact gtggctgcac catctgtctt catcttcccg      420
ccatctgatg agcagttgaa atctggaact gcctctgttg tgtgcctgct gaataacttc      480
tatcccagag aggccaaagt acagtggaag gtggataacg ccctccaatc gggtaactcc      540
caggagagtg tcacagagca ggacagcaag gacagcacct acagcctcag cagcaccctg      600
acgctgagca aagcagacta cgagaaacac aaagtctacg cctgcgaagt cacccatcag      660
ggcctgagct cgcccgtcac aaagagcttc aacaggggag agtgttag                  708
```

<210> SEQ ID NO 134
<211> LENGTH: 1431
<212> TYPE: DNA
<213> ORGANISM: Artificial Sequence
<220> FEATURE:
<223> OTHER INFORMATION: Antibody 4 heavy chain

<400> SEQUENCE: 134

```
atggagtttg gcctgagctg ggttttcctc gttgctcttt taagaggtgt ccagtgtcag       60
gtgcagctgg tggagtctgg gggaggcgtg gtccagcctg gaggtccct gagactctcc       120 tgtgcagcgt ctggattcac cttcagtagg tttggcatcc actgggtccg ccaggctcca      180
ggcaaggggc tggagtggat ggcagttata tggtacgatg gaagtaataa attctatgca      240
gactccgtga agggccgatt caccatctcc agagacaatt ccaagaacac ggtttatctg      300
caaatgaaca gcctcagagc cgaggacacg gctgtctatt actgtgcgaa agattcccgc      360
ggatattgta gtagtatcat ttgttttgag ggggacttg acaactgggg ccagggaacc      420
ctggtcaccg tctcctcagc ctccaccaag ggcccatcgg tcttcccct ggcaccctcc      480
```

| | |
|---|---|
| tccaagagca cctctggggg cacagcggcc ctgggctgcc tggtcaagga ctacttcccc | 540 |
| gaaccggtga cggtgtcgtg gaactcaggc gccctgacca gcggcgtgca caccttcccg | 600 |
| gctgtcctac agtcctcagg actctactcc ctcagcagcg tggtgaccgt gccctccagc | 660 |
| agcttgggca cccagaccta catctgcaac gtgaatcaca agcccagcaa caccaaggtg | 720 |
| gacaagagag ttgagcccaa atcttgtgac aaaactcaca catgcccacc gtgcccagca | 780 |
| cctgaactcc tggggggacc gtcagtcttc ctcttccccc caaaacccaa ggacaccctc | 840 |
| atgatctccc ggacccctga ggtcacatgc gtggtggtgg acgtgagcca cgaagaccct | 900 |
| gaggtcaagt tcaactggta cgtggacggc gtggaggtgc ataatgccaa gacaaagccg | 960 |
| cgggaggagc agtacaacag cacgtaccgt gtggtcagcg tcctcaccgt cctgcaccag | 1020 |
| gactggctga atggcaagga gtacaagtgc aaggtctcca acaaagccct cccagccccc | 1080 |
| atcgagaaaa ccatctccaa agccaagggg cagccccgag aaccacaggt gtacaccctg | 1140 |
| cccccatccc gggatgagct gaccaagaac caggtcagcc tgacctgcct ggtcaaaggc | 1200 |
| ttctatccca gcgacatcgc cgtggagtgg gagagcaatg ggcagccgga gaacaactac | 1260 |
| aagaccacgc ctcccgtgct ggactccgac ggctcctttt tcctttacag caagctcacc | 1320 |
| gtggacaaga gcaggtggca gcaggggaac gtcttttcat gctccgtgat gcatgagggt | 1380 |
| ttgcacaacc actacacgca gaagagcctc tccctgtttc cgggtaaatg a | 1431 |

<210> SEQ ID NO 135
<211> LENGTH: 648
<212> TYPE: DNA
<213> ORGANISM: Artificial Sequence
<220> FEATURE:
<223> OTHER INFORMATION: Antibody 5 light chain

<400> SEQUENCE: 135

| | |
|---|---|
| gagattgtgt tgactcagtc tccaggcacc ctgtctgtgt ctccagggga aagagccacc | 60 |
| ctctcctgca gggccagtcg cgcgcgttggc agcacctact tagcctggta ccagcagaaa | 120 |
| cctggccagg ctcccaggcg cctcatctat ggtgcatcca gcagggccgc tggcatccca | 180 |
| gacaggttca gtggcactgg gtctgggaca gacttcactc tcaccatcag cagggtggac | 240 |
| cctgaagatt ttgcggtata ttactgtcag cagtatgctg cctcaccgtg acgttcggc | 300 |
| caagggacca cggtggagat caaacgaact gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca agcagactac gagaaacac aaagtctacg cctgcgaagt cacccatcag | 600 |
| ggcctgagct cgcccgtcac aaagagcttc aacagggag agtgttag | 648 |

<210> SEQ ID NO 136
<211> LENGTH: 1371
<212> TYPE: DNA
<213> ORGANISM: Artificial Sequence
<220> FEATURE:
<223> OTHER INFORMATION: Antibody 5 heavy chain

<400> SEQUENCE: 136

| | |
|---|---|
| caggttcagc tggtgcagtc tggaggtgag ctgaagaagc ctggggcctc agtgagggtc | 60 |
| tcctgtaagg cttctggcta caccttacc acctatggca tcagctgggt gcgacaggcc | 120 |
| cctggacaag gccttgagtg ggtgggatgg atcagcgctt atactggaaa tacagactat | 180 |

```
gcacagaagg tccagggcag agtaaccatg accacggaca catccacgag cacagcctac    240
atggagctga ggagcctcac atctgacgac acggccgtct attactgtgc gagagataag    300
gtccaggggc gcgttgaagc gggaagtggg ggccggcatg actactgggg ccagggaacc    360
ctggtcaccg tctcctcagc ctccaccaag ggcccatcgg tcttcccct ggcaccctcc    420 tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactct ctcagcagcg tggtgaccgt gccctccagc    600
agcttgggca cccagaccta catctgcaac gtgaatcaca agcccagcaa caccaargtg    660
gacaagaaag ttgagcccaa atcttgtgac aaaactcaca catgcccacc gtgcccagca    720
cctgaactcc tggggggacc gtcagtcttc ctcttcccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggatgagct gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctacag caagctcacc    1260
gtggacaaga gcaggtggca gcaggggaac gtcttctcat gctccgtgat gcatgagggt    1320
ctgcacaacc actacacgca gaagagcctc tccctgtctc cgggtaaatg a           1371

<210> SEQ ID NO 137
<211> LENGTH: 648
<212> TYPE: DNA
<213> ORGANISM: Artificial Sequence
<220> FEATURE:
<223> OTHER INFORMATION: Antibody 6 light chain

<400> SEQUENCE: 137
gaagttgtgt tgacgcagtc tcccggcacc ctgactttgc ctccagggga cagagccacc    60
ctctcctgca gggccagtca cagtgttggc agcacctaca tagcctggtt tcagcagaag    120
tctggccagg ctcccaggcg cctcatctat ggtgcatcca cagggccact gacatccca    180 gacaggttca gtggcagtgg gtccgggaca gacttcactc tcaccatcag agactggag    240 cctgaagatt ctgcagtgta ctactgtcag cagtttagtg tttcaccgtg acgttcggc    300 caagggacca gggtggaaat caagcgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacagggag agtgttag                 648

<210> SEQ ID NO 138
<211> LENGTH: 1371
<212> TYPE: DNA
<213> ORGANISM: Artificial Sequence
<220> FEATURE:
```

<223> OTHER INFORMATION: Antibody 6 heavy chain

<400> SEQUENCE: 138

```
caggttcagc tggtccagtc tggagtagag gtgaagaagc ctggggcctc agtgaaggtc      60
tcctgcaaga cttctggtta tccgttttcc acttatggag tcagctgggt ccgacaggcc     120
cctggacaag ggcttgagtg ggtgggatgg atcagcggtt atactggtat cacagactac     180
gcacagaagt ctcagggcag agtcactctg acgacagacg caagcacggc caccgccttc     240
ttggagctga ggagtctgag gcctgacgac acggccacct attttgtgc gagagacaaa      300
gtgcaggggc gcgttgaagc gggatctggg ggtcgtcacg actactgggg cagggaacc      360
ctggtcatcg tctcctcagc ctccaccaag ggcccatcgg tcttcccct ggcaccctcc      420
tccaagagca cctctggggg cacagcggcc ctgggctgcc tggtcaagga ctacttcccc     480
gaaccggtga cggtgtcgtg aactcaggc gccctgacca gcggcgtgca caccttcccg      540
gctgtcctac agtcctcagg actctactcc ctcagcagcg tggtgaccgt gccctccagc     600
agcttgggca cccagaccta catctgcaac gtgaatcaca agcccagcaa caccaaggtg     660
gacaagaaag ttgagcccaa atcttgtgac aaaactcaca catgcccacc gtgcccagca     720
cctgaactcc tggggggacc gtcagtcttc ctcttccccc caaaacccaa ggacaccctc     780
atgatctccc ggaccctga ggtcacatgc gtggtggtgg acgtgagcca cgaagaccct      840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggatgagct gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct cctctacag caagctcacc    1260
gtggacaaga gcaggtggca gcaggggaac gtcttctcat gctccgtgat gcatgagggt    1320
ctgcacaacc actacacgca gaagagcctc tccctgtctc cgggtaaatg a             1371
```

<210> SEQ ID NO 139
<211> LENGTH: 648
<212> TYPE: DNA
<213> ORGANISM: Artificial Sequence
<220> FEATURE:
<223> OTHER INFORMATION: Antibody 7 light chain

<400> SEQUENCE: 139

```
gaagttgtgt tgacgcagtc tcccggcacc ctggctttgc ctccagggga aagagccacc      60
ctctcctgca gggccagtca cagtattggc agcacctaca tagcctggta tcagcagaag     120
tctggccagg ctcccaggcg cctcatctat ggtgcatcca cagggcctc tgacatccca      180
gacaggttca gtggcagtgg gtccgggaca gacttcactc tcaccatcag agactggag      240
cctgaagatt ctgcagtgta ttactgtcag cagtttagtg tttcaccgtg gacgttcggc     300
caagggacca gggtggaaat caagcgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg cctccaatc gggtaactcc      480
caggagagtg tcacagagca ggacagcaag gacagcacct acagcctcag cagcaccctg     540
acgctgagca aagcagacta cgagaaacac aaagtctacg cctgcgaagt cacccatcag     600
```

```
ggcctgagct cgcccgtcac aaagagcttc aacaggggag agtgttag            648

<210> SEQ ID NO 140
<211> LENGTH: 1371
<212> TYPE: DNA
<213> ORGANISM: Artificial Sequence
<220> FEATURE:
<223> OTHER INFORMATION: Antibody 7 heavy chain

<400> SEQUENCE: 140
caggttcagc tggtgcagtc tggagctgag gtgaagaagc ctggggcctc agtgaaggtc     60
tcctgcaaga cttctggtta ttccttttcc acttatggag tcagctgggt ccgacaggcc    120
cctggacaag gcttgagtg gtgggatgg atcagcggtt acactggtat cacagactac     180
gcacagaagt tcagggcag agtcactctg accacagacg caaccacggc caccgccttc    240
ctggagctga ggagtctgag acctgacgac acggccacct atttctgtgc gagagataag    300 gtgcagggc gcgttgaagt gggatctggg ggtcgtcatg actactgggg acagggaacc    360
ctggtcatcg tctcctcagc ctccaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggg gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtacaccctg   1080
cccccatccc gggatgagct gaccaagaac caggtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctacag caagctcacc   1260
gtggacaaga gcaggtggca gcaggggaac gtcttctcat gctccgtgat gcatgagggt   1320
ctgcacaacc actacacgca gaagagcctc tccctgtctc cgggtaaatg a            1371
```

STABLE LIQUID PHARMACEUTICAL FORMULATION OF ANTI-INFLUENZA VIRUS ANTIBODY

CROSS-REFERENCE TO RELATED APPLICATIONS

This application is a national phase entry under 35 U.S.C. § 371 of International Patent Application PCT/KR2017/008605, filed Aug. 9, 2017, designating the United States of America and published as International Patent Publication WO 2018/030777 A1 on Feb. 15, 2018, which claims the benefit under Article 8 of the Patent Cooperation Treaty to Korean Patent Application Serial No. 10-2016-0101719, filed Aug. 10, 2016.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

This disclosure relates to a stable liquid pharmaceutical formulation comprising an anti-influenza virus antibody.

BACKGROUND

Influenza, a respiratory illness caused by infection with influenza viruses, is prevalent in winter months every year. Particularly, elders or infants are highly susceptible to influenza. Influenza virus is divided into three types: influenza A, B and C. Of these types, influenza A and B affect humans or animals. Influenza A virus can be subdivided into different subtypes (H1N1, H3N2, etc.) based on hemagglutinin (HA) and neuraminidase (NA), which are antigens on the virus surface, and influenza B virus is not classified into subtypes. Through combinations of 17 HA subtypes and 10 NA subtypes of influenza A virus, known to date, viruses of various subtypes may occur.

Influenza virus genes are composed of several fragments. When a single host is infected simultaneously with two or more different influenza viruses, an influenza virus of a new subtype may occur through gene rearrangement. This antigenic shift cannot be predicted, and thus is indefensible by current vaccines. Thus, to provide protection against such new influenza viruses, therapeutic agents against a broader spectrum of influenza viruses are urgently required.

As novel therapeutic agents against influenza viruses, antibodies disclosed in Korean Patent Application No. 10-2011-0020061 and Korean Patent Application No. 10-2012-0107512 showed neutralizing effects against major phylogeny group 1 (H1, H2, H5, and H9) and phylogeny group 2 (H3, and H7). Furthermore, Korean Patent Application No. 10-2014-0036601 discloses that a composition containing two or more different antibodies disclosed in the above-mentioned Korean Patent Applications showed preventive and therapeutic effects against influenza viruses belonging to phylogeny groups 1 and 2.

In order to use the anti-influenza virus antibodies having excellent therapeutic and preventive effects as liquid pharmaceutical formulations, it is necessary to develop stable formulations in which the antibody is stable at low temperature (5° C.), normal temperature (25° C.) and high temperature (40° C.) while the aggregation and degradation of the antibody is minimized.

Because antibodies are larger and more complex than traditional organic and inorganic drugs, antibody compositions have special problems. Antibody stability can be affected by such factors as ionic strength, pH, temperature, repeated cycles of freeze/thaw, antibody concentration and shear forces. Active antibodies may be lost as a result of physical instabilities, including denaturation, aggregation (both soluble and insoluble aggregate formation), precipitation and adsorption as well as chemical instabilities, including racemization, beta-elimination or disulfide exchange, hydrolysis, deamidation, and oxidation. Any of these instabilities can potentially result in the formation of antibody by-products or derivatives having lowered biological activity, increased toxicity, and/or increased immunogenicity.

While the prior art indicates numerous examples of excipients that can be suitably employed to create stable liquid pharmaceutical formulation of antibody, it is practically impossible to predict the kinds and amounts of excipients, which should be added to overcome the particular instability problems that a particular antibody may have, in formulation development, because antibodies have their characteristic physical/chemical properties. Furthermore, it is difficult to find optimal conditions, such as antibody concentration, pH and/or concentration of other excipients, which that keep a particular antibody chemically and biologically stable in a composition comprising the antibody.

In addition, finding suitable excipients and optimal conditions for formulating two or more different antibodies and demonstrating the stability thereof are several-fold difficult compared to formulating a single antibody, because the stability of each antibody should be proven and the stability of the composition containing the antibodies should also be proven.

Until now, a prior art document that discloses a stable liquid pharmaceutical formulation comprising an anti-influenza virus antibody has not been found.

Accordingly, there existed a need for a stable liquid pharmaceutical formulation comprising an anti-influenza virus antibody and also a need for a composition for diagnosing, preventing or treating more diverse influenza virus subtypes, which contains a single anti-influenza antibody or two or more different anti-influenza virus antibodies and is stable even upon long-term storage.

BRIEF SUMMARY

Technical Problem

Accordingly, applicants have made efforts to solve the above-described problems, and have found that an antibody or a mixture of two or more different anti-influenza virus antibodies, confirmed to have preventive or therapeutic effects against influenza viruses, is stable at low temperature (5° C.), normal temperature (25° C.) and high temperature (40° C.) and has long-term storage stability.

Therefore, a stable liquid pharmaceutical formulation comprising an anti-influenza virus antibody or a mixture of two or more different anti-influenza virus antibodies is disclosed herein.

A stable liquid pharmaceutical formulation comprising an anti-influenza virus antibody or a mixture of two or more different anti-influenza virus antibodies while, at the same time, being highly stable upon storage at low temperature (5° C.), normal temperature (25° C.) and high temperature (40° C.) and having excellent long-term (12 months) storage stability is disclosed.

A stable liquid pharmaceutical formulation is provided that comprises an anti-influenza virus antibody or a mixture of two or more different anti-influenza virus antibodies, which may be administered intravenously, intramuscularly, transdermally, subcutaneously, intraperitoneally, topically, or a combination thereof.

Technical Solution

A stable liquid pharmaceutical formulation comprising: (A) an anti-influenza virus antibody or a mixture of two or more different anti-influenza virus antibodies; (B) a surfactant; (C) a sugar or its derivative; and (D) an amino acid is disclosed herein.

In one embodiment of the disclosure, the anti-influenza virus antibody or the mixture of two or more different anti-influenza virus antibodies (A) may comprise an antibody that binds to an epitope in the hemagglutinin (HA) protein of influenza A virus.

In one embodiment of this disclosure, the antibody may bind to an epitope in the stem region of the hemagglutinin (HA) protein of influenza A virus.

In one embodiment of the disclosure, the epitope for the antibody may comprise: i) any one or more amino acid residues selected from the group consisting of amino acid residues at positions 18, 25, 27, 32, 33, 38, 40, 54, 55, 278, 291, 292, 310, 311, 312 and 318 of a HA1 polypeptide; and ii) any one or more amino acid residues selected from the group consisting of amino acid residues at positions 18, 19, 20, 21, 38, 39, 41, 42, 45, 46, 48, 49, 52, 53, 56, 57, 58, 60 and 99 of a HA2 polypeptide.

In one embodiment of the disclosure, the epitope may comprise the amino acid residue at position 318 of the HA1 polypeptide, and comprise the amino acid residues at positions 41, 42, 45, 48, 49, 52 and 53 of the HA2 polypeptide.

In one embodiment of this disclosure, the epitope may comprise the amino acid residues at positions 18, 38, 40, 291, 292 and 318 of the HA1 polypeptide. Furthermore, the epitope may comprise the amino acid residues at positions 18, 19, 20, 21, 41, 42, 45, 48, 49, 52 and 53 of the HA2 polypeptide. The epitope may comprise the amino acid residues at positions 18, 38, 40, 291, 292 and 318 of the HA1 polypeptide, and comprise the amino acid residues at positions 18, 19, 20, 21, 41, 42, 45, 48, 49, 52 and 53 of the HA2 polypeptide.

In one embodiment of the disclosure, the epitope may comprise the amino acid residues at positions 278 and 318 of the HA1 polypeptide. The epitope may comprise the amino acid residues at positions 38, 39, 41, 42, 45, 48, 49, 52 and 53 of the HA2 polypeptide. The epitope may comprise the amino acid residues at the positions of the HA1 polypeptide and/or HA2 polypeptide of a first monomer of HA, and further comprise the amino acid residues at positions 25, 32 and 33 of the HA1 polypeptide of a second monomer adjacent to the first monomer.

In one embodiment of the disclosure, the epitope may comprise the amino acid residues at positions 278 and 318 of the HA1 polypeptide, and comprise the amino acid residues at positions 38, 39, 41, 42, 45, 48, 49, 52 and 53 of the HA2 polypeptide. The epitope may comprise the amino acid residues at the positions of the HA1 polypeptide and HA2 polypeptide of a first monomer of HA, and further comprise the amino acid residues at positions 25, 32 and 33 of the HA1 polypeptide of a second monomer adjacent to the first monomer.

In one embodiment of this disclosure, the epitope may comprise the amino acid residues at positions 278 and 318 of the HA1 polypeptide, and comprise the amino acid residues at positions 38, 39, 41, 42, 45, 48, 49, 52, 53, 58 and 99 of the HA2 polypeptide. The epitope may comprise the amino acid residues at the positions of the HA1 polypeptide and HA2 polypeptide of a first monomer of HA, and may further comprise the amino acid residues at positions 25, 27, 32 and 33 of the HA1 polypeptide of a second monomer adjacent to the first monomer.

In one embodiment of the disclosure, the epitope may comprise the amino acid residues at positions 54, 55, 278, 291 and 318 of the HA1 polypeptide, and comprise the amino acid residues at positions 19, 20, 21, 38, 39, 41, 42, 45, 46, 48, 49, 52, 53, 56, 57 and 60 of the HA2 polypeptide. The epitope may comprise the amino acid residues at the positions of the HA1 polypeptide and HA2 polypeptide of a first monomer of HA, and may further comprise the amino acid residues at positions 25, 32, 33, 310, 311 and 312 of the HA1 polypeptide of a second monomer of HA adjacent to the first monomer of HA.

In one embodiment of the disclosure, the anti-influenza virus antibody (A) may comprise any one antibody selected from the group consisting of: i) an antibody comprising a light-chain variable region comprising a CDR1 region of SEQ ID NO: 1, a CDR2 region of SEQ ID NO: 2 and a CDR3 region of SEQ ID NO: 3, and a heavy-chain variable region comprising a CDR1 region of SEQ ID NO: 4, a CDR2 region of SEQ ID NO: 5 and a CDR3 region of SEQ ID NO: 6; ii) an antibody comprising a light-chain variable region comprising a CDR1 region of SEQ ID NO: 7, a CDR2 region of SEQ ID NO: 8 and a CDR3 region of SEQ ID NO: 9, and a heavy-chain variable region comprising a CDR1 region of SEQ ID NO: 10, a CDR2 region of SEQ ID NO: 11 and a CDR3 region of SEQ ID NO: 12; iii) an antibody comprising a light-chain variable region comprising a CDR1 region of SEQ ID NO: 13, a CDR2 region of SEQ ID NO: 14 and a CDR3 region of SEQ ID NO: 15, and a heavy-chain variable region comprising a CDR1 region of SEQ ID NO: 16, a CDR2 region of SEQ ID NO: 17 and a CDR3 region of SEQ ID NO: 18; iv) an antibody comprising a light-chain variable region comprising a CDR1 region of SEQ ID NO: 19, a CDR2 region of SEQ ID NO: 20 and a CDR3 region of SEQ ID NO: 21, and a heavy-chain variable region comprising a CDR1 region of SEQ ID NO: 22, a CDR2 region of SEQ ID NO: 23 and a CDR3 region of SEQ ID NO: 24; v) an antibody comprising a light-chain variable region comprising a CDR1 region of SEQ ID NO: 25, a CDR2 region of SEQ ID NO: 26 and a CDR3 region of SEQ ID NO: 27, and a heavy-chain variable region comprising a CDR1 region of SEQ ID NO: 28, a CDR2 region of SEQ ID NO: 29 and a CDR3 region of SEQ ID NO: 30; vi) an antibody comprising a light-chain variable region comprising a CDR1 region of SEQ ID NO: 31, a CDR2 region of SEQ ID NO: 32 and a CDR3 region of SEQ ID NO: 33, and a heavy-chain variable region comprising a CDR1 region of SEQ ID NO: 34, a CDR2 region of SEQ ID NO: 35 and a CDR3 region of SEQ ID NO: 36; and vii) an antibody comprising a light-chain variable region comprising a CDR1 region of SEQ ID NO: 37, a CDR2 region of SEQ ID NO: 38 and a CDR3 region of SEQ ID NO: 39, and a heavy-chain variable region comprising a CDR1 region of SEQ ID NO: 40, a CDR2 region of SEQ ID NO: 41 and a CDR3 region of SEQ ID NO: 42.

In one embodiment of this disclosure, the anti-influenza virus antibody (A) may comprise any one antibody selected from the group consisting of: i) an antibody comprising a light-chain variable region having a sequence identity of 95% or more to the light-chain variable region of a polypeptide sequence of SEQ ID NO: 43, and a heavy-chain variable region having a sequence identity of 95% or more to the heavy-chain variable region of a polypeptide sequence of SEQ ID NO: 44; ii) an antibody comprising a light-chain variable region having a sequence identity of 95% or more to the light-chain variable region of a polypeptide sequence of SEQ ID NO: 45, and a heavy-chain variable region having a sequence identity of 95% or more to the heavy-chain variable region of a polypeptide sequence of SEQ ID NO: 46; iii) an antibody comprising a light-chain variable region having a sequence identity of 95% or more to the light-chain variable region of a polypeptide sequence of SEQ ID NO: 47, and a heavy-chain variable region having a sequence identity of 95% or more to the heavy-chain variable region of a polypeptide sequence of SEQ ID NO: 48; iv) an antibody comprising a light-chain variable region having a sequence identity of 95% or more to the light-chain variable region of a polypeptide sequence of SEQ ID NO: 49, and a heavy-chain variable region having a sequence identity of 95% or more to the heavy-chain variable region of a polypeptide sequence of SEQ ID NO: 50; v) an antibody comprising a light-chain variable region having a sequence identity of 95% or more to the light-chain variable region of a polypeptide sequence of SEQ ID NO: 51, and a heavy-chain variable region having a sequence identity of 95% or more to the heavy-chain variable region of a polypeptide sequence of SEQ ID NO: 52; vi) an antibody comprising a light-chain variable region having a sequence identity of 95% or more to the light-chain variable region of a polypeptide sequence of SEQ ID NO: 53, and a heavy-chain variable region having a sequence identity of 95% or more to the heavy-chain variable region of a polypeptide sequence of SEQ ID NO: 54; and vii) an antibody comprising a light-chain variable region having a sequence identity of 95% or more to the light-chain variable region of a polypeptide sequence of SEQ ID NO: 55, and a heavy-chain variable region having a sequence identity of 95% or more to the heavy-chain variable region of a polypeptide sequence of SEQ ID NO: 56.

In one embodiment of the disclosure, the anti-influenza virus antibody (A) may comprise any one antibody selected from the group consisting of: i) an antibody comprising a light chain having a sequence identity of 95% or more to the light chain of a polypeptide sequence of SEQ ID NO: 57, and a heavy chain having a sequence identity of 95% or more to the heavy chain of a polypeptide sequence of SEQ ID NO: 58; ii) an antibody comprising a light chain having a sequence identity of 95% or more to the light chain of a polypeptide sequence of SEQ ID NO: 59, and a heavy chain having a sequence identity of 95% or more to the heavy chain of a polypeptide sequence of SEQ ID NO: 60; iii) an antibody comprising a light chain having a sequence identity of 95% or more to the light chain of a polypeptide sequence of SEQ ID NO: 61, and a heavy chain having a sequence identity of 95% or more to the heavy chain of a polypeptide sequence of SEQ ID NO: 62; iv) an antibody comprising a light chain having a sequence identity of 95% or more to the light chain of a polypeptide sequence of SEQ ID NO: 63, and a heavy chain having a sequence identity of 95% or more to the heavy chain of a polypeptide sequence of SEQ ID NO: 64; v) an antibody comprising a light chain having a sequence identity of 95% or more to the light chain of a polypeptide sequence of SEQ ID NO: 65, and a heavy chain having a sequence identity of 95% or more to the heavy chain of a polypeptide sequence of SEQ ID NO: 66; vi) an antibody comprising a light chain having a sequence identity of 95% or more to the light chain of a polypeptide sequence of SEQ ID NO: 67, and a heavy chain having a sequence identity of 95% or more to the heavy chain of a polypeptide sequence of SEQ ID NO: 68; and vii) an antibody comprising a light chain having a sequence identity of 95% or more to the light chain of a polypeptide sequence of SEQ ID NO: 69, and a heavy chain having a sequence identity of 95% or more to the heavy chain of a polypeptide sequence of SEQ ID NO: 70.

In one embodiment of the disclosure, the mixture of two or more different anti-influenza virus antibodies (A) may comprise: i) an antibody comprising a light-chain variable region comprising a CDR1 region of SEQ ID NO: 1, a CDR2 region of SEQ ID NO: 2 and a CDR3 region of SEQ ID NO: 3, and a heavy-chain variable region comprising a CDR1 region of SEQ ID NO: 4, a CDR2 region of SEQ ID NO: 5 and a CDR3 region of SEQ ID NO: 6; and ii) an antibody comprising a light-chain variable region comprising a CDR1 region of SEQ ID NO: 7, a CDR2 region of SEQ ID NO: 8 and a CDR3 region of SEQ ID NO: 9, and a heavy-chain variable region comprising a CDR1 region of SEQ ID NO: 10, a CDR2 region of SEQ ID NO: 11 and a CDR3 region of SEQ ID NO: 12.

In one embodiment of this disclosure, the mixture of two or more different anti-influenza virus antibodies (A) may comprise: i) an antibody comprising a light-chain variable region having a sequence identity of 95% or more to the light-chain variable region of a polypeptide sequence of SEQ ID NO: 43, and a heavy-chain variable region having a sequence identity of 95% or more to the heavy-chain variable region of a polypeptide sequence of SEQ ID NO: 44; and ii) an antibody comprising a light-chain variable region having a sequence identity of 95% or more to the light-chain variable region of a polypeptide sequence of SEQ ID NO: 45, and a heavy-chain variable region having a sequence identity of 95% or more to the heavy-chain variable region of a polypeptide sequence of SEQ ID NO: 46.

In one embodiment of the disclosure, the mixture of two or more different anti-influenza virus antibodies (A) may comprise: i) an antibody comprising a light chain having a sequence identity of 95% or more to the light chain of a polypeptide sequence of SEQ ID NO: 57, and a heavy chain having a sequence identity of 95% or more to the heavy chain of a polypeptide sequence of SEQ ID NO: 58; and ii) an antibody comprising a light chain having a sequence identity of 95% or more to the light chain of a polypeptide sequence of SEQ ID NO: 59, and a heavy chain having a sequence identity of 95% or more to the heavy chain of a polypeptide sequence of SEQ ID NO: 60.

In one embodiment of the disclosure, the anti-influenza virus antibody (A) may comprise: MHAA4549A antibody (Genentech, Inc.); MEDI8852 antibody (Medimmune, Inc.); CR6261 antibody, CR8020 antibody, CR9114 antibody, CR8033 antibody and CR8071 antibody, which are commercially available from Crucell; F10 antibody (Dana-Farber Cancer Institute); VIS410 antibody (Visterra); TCN-032 antibody (Theraclone Sciences, Inc.); and/or FI6 antibody (Swiss Federal Institute of Technology (IRB)).

In one embodiment of the disclosure, when the mixture of two or more different anti-influenza virus antibodies (A) is a mixture of two different antibodies, the mixing ratio between the two different antibodies may be 9:1 to 1:9.

In one embodiment of the disclosure, the concentration of the anti-influenza virus antibody or the mixture of two or more different anti-influenza virus antibodies (A) may be 10 to 150 mg/mL.

In one embodiment of the disclosure, the surfactant (B) may comprise polysorbate, poloxamer, or a mixture thereof.

In one embodiment of this disclosure, the surfactant (B) may comprise polysorbate 20, polysorbate 40, polysorbate 60, polysorbate 80, or a mixture of two or more thereof.

In one embodiment of the disclosure, the surfactant (B) may comprise polysorbate 80.

In one embodiment of the disclosure, the concentration of the surfactant (B) may be 0.01 to 1.0% (w/v).

In one embodiment of the disclosure, the sugar (C) may comprise a monosaccharide, a disaccharide, an oligosaccharide, a polysaccharide, or a mixture of two or more thereof.

In one embodiment of the disclosure, the sugar derivative (C) may comprise sugar alcohol, sugar acid, or a mixture thereof.

In one embodiment of this disclosure, the sugar (C) may comprise a monosaccharide, a disaccharide, an oligosaccharide, a polysaccharide, or a mixture of two or more thereof, and the sugar derivative (C) may comprise sugar alcohol, sugar acid, or a mixture thereof.

In one embodiment of the disclosure, the sugar or its derivative (C) may comprise sorbitol, mannitol, trehalose, sucrose, or a mixture of two or more thereof.

In one embodiment of the disclosure, the concentration of the sugar or its derivative (C) may be 0.1 to 15% (w/v).

In one embodiment of the disclosure, the amino acid (D) may comprise free amino acid, amino acid salt, or a mixture thereof.

In one embodiment of the disclosure, the amino acid (D) may comprise aspartic acid, histidine, lysine, arginine, or a salt thereof.

In one embodiment of the disclosure, the amino acid (D) may comprise histidine, histidine salt, or a mixture thereof.

In one embodiment of the disclosure, the concentration of the amino acid (D) may be 1 to 20 mM.

In one embodiment of the disclosure, the pH of the stable liquid pharmaceutical formulation may be 5.5 to 6.5.

In one embodiment of this disclosure, the stable liquid pharmaceutical formulation may have an antibody monomer purity of 95% or higher as measured after 6 weeks of storage at 40±2° C.

In one embodiment of the disclosure, the stable liquid pharmaceutical formulation may have an antibody monomer purity of 95% or higher as measured after 3 months or more of storage at 5±3° C.

In one embodiment of the disclosure, the stable liquid pharmaceutical formulation may have an antibody monomer purity of 95% or higher as measured after 6 months or more of storage at 5±3° C.

In one embodiment of the disclosure, the stable liquid pharmaceutical formulation may be administered intravenously, intramuscularly, transdermally, subcutaneously, intraperitoneally, topically, or a combination thereof.

In one embodiment of the disclosure, the stable liquid pharmaceutical formulation is filled in a pre-filled syringe.

In one embodiment of the disclosure, the pre-filled syringe is included in an auto-injector.

In one embodiment of the disclosure, a kit may comprise the stable liquid pharmaceutical formulation and a container.

In one embodiment of the disclosure, the stable liquid pharmaceutical formulation may be for diagnosis, prevention or treatment of influenza virus.

In one embodiment of this disclosure, there is provided a method for preparing the stable liquid pharmaceutical formulation.

Advantageous Effects

The stable liquid pharmaceutical formulation comprising an anti-influenza virus antibody according to this disclosure is highly stable upon storage at low temperature (5° C.), normal temperature (25° C.) and high temperature (40° C.), has excellent long-term (12 months) storage stability, and may be administered intravenously, intramuscularly, transdermally, subcutaneously, intraperitoneally, topically, or a combination thereof.

Stable Liquid Pharmaceutical Formulation

A stable liquid pharmaceutical formulation according to this disclosure may comprise: (A) an anti-influenza virus antibody or a mixture of two or more different anti-influenza virus antibodies; (B) a surfactant; (C) a sugar or its derivative; and (D) an amino acid.

(A) an Anti-Influenza Virus Antibody or a Mixture of Two or More Different Anti-Influenza Virus Antibodies As used herein, the term "antibody" is used in its broadest sense and may include polyclonal antibodies, monoclonal antibodies, recombinant antibodies, single-chain antibodies, hybrid antibodies, chimeric antibodies, humanized antibodies, human antibodies, and fragments thereof. Other naturally occurring antibodies having an altered structure, for example, camelid antibodies, are also included in this definition. The term "intact antibody" refers to immunoglobulin molecules comprised of four polypeptide chains, two heavy chains and two light chains inter-connected by disulfide bonds. Antigen-binding fragments include, inter alia, Fab, F(ab'), F(ab')2, Fv, dAb, Fd, complementarity-determining region (CDR) fragments, single-chain antibodies (scFv), bivalent single-chain antibodies, single-chain phage antibodies, diabodies, triabodies, tetrabodies, (poly)peptides that contain at least one fragment of an immunoglobulin that is sufficient to confer specific antigen binding to the (poly) peptide, etc. Each heavy chain is comprised of a heavy-chain variable region and a heavy-chain constant region. The heavy-chain constant region is comprised of three domains (CH1, CH2 and CH3). Each light chain is comprised of a light-chain variable region and a light-chain constant region. The light-chain constant region is comprised of one domain (CL). The heavy-chain variable region and the light-chain variable region can be further subdivided into regions of hypervariability, termed "complementarity-determining regions (CDR)," interspersed with regions that are more conserved, termed "framework regions (FR)." Each of the heavy-chain variable region and the light-chain variable region is composed of three CDRs and four FRs, which are arranged from amino-terminus to carboxy-terminus in the following order: FR1, CDR1, FR2, CDR2, FR3, CDR3, and FR4.

In the present disclosure, the complementarity-determining regions (CRDs) of variable domains were determined using a conventional method according to the system designed by Kabat et al. (see Kabat et al., Sequences of Proteins of Immunological Interest ($5^{th}$), National Institutes of Health, Bethesda, MD. (1991)). CDR numbering used in this disclosure was performed according to the Kabat method, but the disclosure also encompasses antibodies comprising CDRs determined by other methods, including the IMGT method, the Chothia method, the AbM method, and the like.

The antibodies according to the disclosure include functional variants of the antibodies. Functional variants of antibodies are considered to be functional variants of the antibodies according to the disclosure, if the variants are capable of competing for specifically binding to influenza viruses with the antibodies of the disclosure Functional variants include, but are not limited to, derivatives that are substantially similar in primary structural sequence. Alternatively, functional variants can be antibodies comprising an amino acid sequence containing substitutions, insertions, deletions or combinations thereof of one or more amino acids compared to the amino acid sequences of the parental antibodies. Furthermore, functional variants can comprise truncations of the amino acid sequence at either or both the amino or carboxyl termini. Functional variants according to the disclosure may have the same or different, either higher or lower, binding affinities compared to the parental antibody but are still capable of binding to influenza viruses. Functional variants intended to fall within the scope of this disclosure may have an amino acid sequence identity of about 50 to 99%, about 60 to 99%, about 80 to 99%, about 90 to 99%, about 95 to 99%, or about 97 to 99% with the antibodies as disclosed herein. Computer algorithms such as inter alia Gap or Bestfit known to a person skilled in the art can be used to optimally align amino acid sequences to be compared and to define similar or identical amino acid residues. Functional variants can be obtained by altering the parental antibodies or parts thereof by general molecular biology methods known in the art including, PCR, oligonucleotide-directed mutagenesis, and site-directed mutagenesis, or can be obtained by organic synthesis methods, but are not limited thereto.

Depending on the constant domain or region of their heavy chains, "antibodies" in this disclosure can be assigned to different classes, but are not limited thereto. For example, there are five major classes of antibodies: IgA, IgD, IgE, IgG, and IgM; and several of these may be further divided into subclasses (isotypes), e.g., IgG1, IgG2, IgG3, IgG4, IgA1, and IgA2.

The "epitope" in this disclosure is a region of an antigen that is bound by an antibody targeting the antigen, and it includes specific amino acids coming into direct contact with the antibody, but is not limited thereto. For example, the epitope may include chemically active surface groupings of molecules such as amino acids, sugar side chains, phosphoryl, or sulfonyl, and may have specific three dimensional structural characteristics and/or specific charge characteristics.

The term "influenza A viruses," as used herein, refers to enveloped viruses belonging to the family Orthomyxoviridae and having a genome composed of eight negative-sense, single-stranded RNA (ribonucleic acid) segments. These influenza viruses are classified into types A, B and C, and the influenza A viruses are further divided into subtypes based on their major surface proteins HA (hemagglutinin) and NA (neuraminidase). 17 HAs and 10 NAs have been reported to date.

As used herein, the term "hemagglutinin" (hereinafter referred to as "HA") indicates the envelope glycoprotein of influenza virus. HA mediates the adsorption and penetration of influenza virus into a host cell. 17 HA subtypes have been reported to date.

"H1 subtypes" described in the disclosure include H1N1, H1N2, H1N3, H1N4, H1N5, H1N6, H1N7, H1N8, H1N9, and H1N10.

"H2 subtypes" described in the disclosure include H2N1, H2N2, H2N3, H2N4, H2N5, H2N6, H2N7, H2N8, H2N9, and H2N10.

"H5 subtypes" described in the disclosure include H5N1, H5N2, H5N3, H5N4, H5N5, H5N6, H5N7, H5N8, H5N9, and H5N10.

"H9 subtypes" described in the disclosure include H9N1, H9N2, H9N3, H9N4, H9N5, H9N6, H9N7, H9N8, H9N9, and H9N10.

"H3 subtypes" described in the disclosure include H3N1, H3N2, H3N3, H3N4, H3N5, H3N6, H3N7, H3N8, H3N9, and H3N10.

"H7 subtypes" described in the disclosure include H7N1, H7N2, H7N3, H7N4, H7N5, H7N6, H7N7, H7N8, H7N9, and H7N10.

In one embodiment of this disclosure, the "antibody" may include an antibody that binds to or neutralizes influenza virus.

In one embodiment of the disclosure, the "mixture of antibodies" may comprise two or more different anti-influenza virus antibodies.

In one embodiment of the disclosure, the anti-influenza virus antibody or the mixture of two or more different anti-influenza virus antibodies may comprise an antibody that binds to influenza A virus.

In another embodiment of the disclosure, the anti-influenza virus antibody or the mixture of two or more different anti-influenza virus antibodies may comprise an antibody that binds to the hemagglutinin (HA) protein of influenza A virus. In still another embodiment of this disclosure, the anti-influenza virus antibody or the mixture of two or more different anti-influenza virus antibodies may comprise an antibody that binds to the stem region of the hemagglutinin (HA) protein of influenza A virus or an epitope thereof.

In one embodiment of the disclosure, the epitope for the antibody may comprise: i) any one or more amino acid residues selected from the group consisting of amino acid residues at positions 18, 25, 27, 32, 33, 38, 40, 54, 55, 278, 291, 292, 310, 311, 312 and 318 of the HA1 polypeptide; and ii) any one or more amino acid residues selected from the group consisting of amino acid residues at positions 18, 19, 20, 21, 38, 39, 41, 42, 45, 46, 48, 49, 52, 53, 56, 57, 58, 60 and 99 of the HA2 polypeptide.

In one embodiment of the disclosure, the epitope may comprise the amino acid residue at position 318 of the HA1 polypeptide, and comprise the amino acid residues at positions 41, 42, 45, 48, 49, 52 and 53 of the HA2 polypeptide.

In one embodiment of the disclosure, the epitope may comprise the amino acid residues at positions 18, 38, 40, 291, 292 and 318 of the HA1 polypeptide. Furthermore, the epitope may comprise the amino acid residues at positions 18, 19, 20, 21, 41, 42, 45, 48, 49, 52 and 53 of the HA2 polypeptide. The epitope may comprise the amino acid residues at positions 18, 38, 40, 291, 292 and 318 of the HA1 polypeptide, and comprise the amino acid residues at positions 18, 19, 20, 21, 41, 42, 45, 48, 49, 52 and 53 of the HA2 polypeptide.

In one embodiment of the disclosure, the epitope may comprise the amino acid residues at positions 278 and 318 of the HA1 polypeptide. The epitope may comprise the amino acid residues at positions 38, 39, 41, 42, 45, 48, 49, 52 and 53 of the HA2 polypeptide. The epitope may comprise the amino acid residues at the positions of the HA1 polypeptide and/or HA2 polypeptide of a first monomer of HA, and may further comprise the amino acid residues at positions 25, 32 and 33 of the HA1 polypeptide of a second monomer adjacent to the first monomer.

In one embodiment of the disclosure, the epitope may comprise the amino acid residues at positions 278 and 318 of the HA1 polypeptide, and comprise the amino acid residues at positions 38, 39, 41, 42, 45, 48, 49, 52 and 53 of the HA2 polypeptide. The epitope may comprise the amino acid residues at the positions of the HA1 polypeptide and HA2 polypeptide of a first monomer of HA, and may further comprise the amino acid residues at positions 25, 32 and 33 of the HA1 polypeptide of a second monomer adjacent to the first monomer.

In one embodiment of this disclosure, the epitope may comprise the amino acid residues at positions 278 and 318 of the HA1 polypeptide, and comprise the amino acid residues at positions 38, 39, 41, 42, 45, 48, 49, 52, 53, 58 and 99 of the HA2 polypeptide. The epitope may comprise the amino acid residues at the positions of the HA1 polypeptide and HA2 polypeptide of a first monomer of HA, and may further comprise the amino acid residues at positions 25, 27, 32 and 33 of the HA1 polypeptide of a second monomer adjacent to the first monomer.

In one embodiment of the disclosure, the epitope may comprise the amino acid residues at positions 54, 55, 278, 291 and 318 of the HA1 polypeptide, and comprise the amino acid residues at positions 19, 20, 21, 38, 39, 41, 42, 45, 46, 48, 49, 52, 53, 56, 57 and 60 of the HA2 polypeptide. The epitope may comprise the amino acid residues at the positions of the HA1 polypeptide and HA2 polypeptide of a first monomer of HA, and may further comprise the amino acid residues at positions 25, 32, 33, 310, 311 and 312 of the HA1 polypeptide of a second monomer of HA adjacent to the first monomer of HA.

In one embodiment of the disclosure, the anti-influenza virus antibodies may include polyclonal antibodies, monoclonal antibodies, recombinant antibodies, single-chain antibodies, hybrid antibodies, chimeric antibodies, humanized antibodies, human antibodies, and fragments thereof.

In another embodiment of this disclosure, the anti-influenza virus antibodies may include human antibodies. In still another embodiment of the disclosure, the anti-influenza virus antibodies may be included in the IgG class of antibodies.

In one embodiment of the disclosure, the anti-influenza virus antibody may comprise any one antibody selected from the group consisting of: i) an antibody comprising a light-chain variable region comprising a CDR1 region of SEQ ID NO: 1, a CDR2 region of SEQ ID NO: 2 and a CDR3 region of SEQ ID NO: 3, and a heavy-chain variable region comprising a CDR1 region of SEQ ID NO: 4, a CDR2 region of SEQ ID NO: 5 and a CDR3 region of SEQ ID NO: 6; ii) an antibody comprising a light-chain variable region comprising a CDR1 region of SEQ ID NO: 7, a CDR2 region of SEQ ID NO: 8 and a CDR3 region of SEQ ID NO: 9, and a heavy-chain variable region comprising a CDR1 region of SEQ ID NO: 10, a CDR2 region of SEQ ID NO: 11 and a CDR3 region of SEQ ID NO: 12; iii) an antibody comprising a light-chain variable region comprising a CDR1 region of SEQ ID NO: 13, a CDR2 region of SEQ ID NO: 14 and a CDR3 region of SEQ ID NO: 15, and a heavy-chain variable region comprising a CDR1 region of SEQ ID NO: 16, a CDR2 region of SEQ ID NO: 17 and a CDR3 region of SEQ ID NO: 18; iv) an antibody comprising a light-chain variable region comprising a CDR1 region of SEQ ID NO: 19, a CDR2 region of SEQ ID NO: 20 and a CDR3 region of SEQ ID NO: 21, and a heavy-chain variable region comprising a CDR1 region of SEQ ID NO: 22, a CDR2 region of SEQ ID NO: 23 and a CDR3 region of SEQ ID NO: 24; v) an antibody comprising a light-chain variable region comprising a CDR1 region of SEQ ID NO: 25, a CDR2 region of SEQ ID NO: 26 and a CDR3 region of SEQ ID NO: 27, and a heavy-chain variable region comprising a CDR1 region of SEQ ID NO: 28, a CDR2 region of SEQ ID NO: 29 and a CDR3 region of SEQ ID NO: 30; vi) an antibody comprising a light-chain variable region comprising a CDR1 region of SEQ ID NO: 31, a CDR2 region of SEQ ID NO: 32 and a CDR3 region of SEQ ID NO: 33, and a heavy-chain variable region comprising a CDR1 region of SEQ ID NO: 34, a CDR2 region of SEQ ID NO: 35 and a CDR3 region of SEQ ID NO: 36; and vii) an antibody comprising a light-chain variable region comprising a CDR1 region of SEQ ID NO: 37, a CDR2 region of SEQ ID NO: 38 and a CDR3 region of SEQ ID NO: 39, and a heavy-chain variable region comprising a CDR1 region of SEQ ID NO: 40, a CDR2 region of SEQ ID NO: 41 and a CDR3 region of SEQ ID NO: 42.

In one embodiment of the disclosure, the anti-influenza virus antibody may comprise any one antibody selected from the group consisting of: i) an antibody comprising a light-chain variable region having a sequence identity of 95% or more to the light-chain variable region of a polypeptide sequence of SEQ ID NO: 43, and a heavy-chain variable region having a sequence identity of 95% or more to the heavy-chain variable region of a polypeptide sequence of SEQ ID NO: 44; ii) an antibody comprising a light-chain variable region having a sequence identity of 95% or more to the light-chain variable region of a polypeptide sequence of SEQ ID NO: 45, and a heavy-chain variable region having a sequence identity of 95% or more to the heavy-chain variable region of a polypeptide sequence of SEQ ID NO: 46; iii) an antibody comprising a light-chain variable region having a sequence identity of 95% or more to the light-chain variable region of a polypeptide sequence of SEQ ID NO: 47, and a heavy-chain variable region having a sequence identity of 95% or more to the heavy-chain variable region of a polypeptide sequence of SEQ ID NO: 48; iv) an antibody comprising a light-chain variable region having a sequence identity of 95% or more to the light-chain variable region of a polypeptide sequence of SEQ ID NO: 49, and a heavy-chain variable region having a sequence identity of 95% or more to the heavy-chain variable region of a polypeptide sequence of SEQ ID NO: 50; v) an antibody comprising a light-chain variable region having a sequence identity of 95% or more to the light-chain variable region of a polypeptide sequence of SEQ ID NO: 51, and a heavy-chain variable region having a sequence identity of 95% or more to the heavy-chain variable region of a polypeptide sequence of SEQ ID NO: 52; vi) an antibody comprising a light-chain variable region having a sequence identity of 95% or more to the light-chain variable region of a polypeptide sequence of SEQ ID NO: 53, and a heavy-chain variable region having a sequence identity of 95% or more to the heavy-chain variable region of a polypeptide sequence of SEQ ID NO: 54; and vii) an antibody comprising a light-chain variable region having a sequence identity of 95% or more to the light-chain variable region of a polypeptide sequence of SEQ ID NO: 55, and a heavy-chain variable region having a sequence identity of 95% or more to the heavy-chain variable region of a polypeptide sequence of SEQ ID NO: 56.

In one embodiment of the disclosure, the anti-influenza virus antibody may comprise any one antibody selected from the group consisting of: i) an antibody comprising a light chain having a sequence identity of 95% or more to the light chain of a polypeptide sequence of SEQ ID NO: 57, and a heavy chain having a sequence identity of 95% or more to the heavy chain of a polypeptide sequence of SEQ ID NO: 58; ii) an antibody comprising a light chain having a sequence identity of 95% or more to the light chain of a polypeptide sequence of SEQ ID NO: 59, and a heavy chain having a sequence identity of 95% or more to the heavy chain of a polypeptide sequence of SEQ ID NO: 60; iii) an antibody comprising a light chain having a sequence identity of 95% or more to the light chain of a polypeptide sequence of SEQ ID NO: 61, and a heavy chain having a sequence identity of 95% or more to the heavy chain of a polypeptide sequence of SEQ ID NO: 62; iv) an antibody comprising a light chain having a sequence identity of 95% or more to the light chain of a polypeptide sequence of SEQ ID NO: 63, and a heavy chain having a sequence identity of 95% or more to the heavy chain of a polypeptide sequence of SEQ ID NO: 64; v) an antibody comprising a light chain having a sequence identity of 95% or more to the light chain of a polypeptide sequence of SEQ ID NO: 65, and a heavy chain having a sequence identity of 95% or more to the heavy chain of a polypeptide sequence of SEQ ID NO: 66; vi) an antibody comprising a light chain having a sequence identity of 95% or more to the light chain of a polypeptide sequence of SEQ ID NO: 67, and a heavy chain having a sequence identity of 95% or more to the heavy chain of a polypeptide sequence of SEQ ID NO: 68; and vii) an antibody comprising a light chain having a sequence identity of 95% or more to the light chain of a polypeptide sequence of SEQ ID NO: 69, and a heavy chain having a sequence identity of 95% or more to the heavy chain of a polypeptide sequence of SEQ ID NO: 70.

In one embodiment of the disclosure, the mixture of two or more different anti-influenza virus antibodies may comprise: i) an antibody comprising a light-chain variable region comprising a CDR1 region of SEQ ID NO: 1, a CDR2 region of SEQ ID NO: 2 and a CDR3 region of SEQ ID NO: 3, and a heavy-chain variable region comprising a CDR1 region of SEQ ID NO: 4, a CDR2 region of SEQ ID NO: 5 and a CDR3 region of SEQ ID NO: 6; and ii) an antibody comprising a light-chain variable region comprising a CDR1 region of SEQ ID NO: 7, a CDR2 region of SEQ ID NO: 8 and a CDR3 region of SEQ ID NO: 9, and a heavy-chain variable region comprising a CDR1 region of SEQ ID NO: 10, a CDR2 region of SEQ ID NO: 11 and a CDR3 region of SEQ ID NO: 12.

In one embodiment of the disclosure, the mixture of two or more different anti-influenza virus antibodies may comprise: i) an antibody comprising a light-chain variable region having a sequence identity of 95% or more to the light-chain variable region of a polypeptide sequence of SEQ ID NO: 43, and a heavy-chain variable region having a sequence identity of 95% or more to the heavy-chain variable region of a polypeptide sequence of SEQ ID NO: 44; and ii) an antibody comprising a light-chain variable region having a sequence identity of 95% or more to the light-chain variable region of a polypeptide sequence of SEQ ID NO: 45, and a heavy-chain variable region having a sequence identity of 95% or more to the heavy-chain variable region of a polypeptide sequence of SEQ ID NO: 46.

In one embodiment of the disclosure, the mixture of two or more different anti-influenza virus antibodies may comprise: i) an antibody comprising a light chain having a sequence identity of 95% or more to the light chain of a polypeptide sequence of SEQ ID NO: 57, and a heavy chain having a sequence identity of 95% or more to the heavy chain of a polypeptide sequence of SEQ ID NO: 58; and ii) an antibody comprising a light chain having a sequence identity of 95% or more to the light chain of a polypeptide sequence of SEQ ID NO: 59, and a heavy chain having a sequence identity of 95% or more to the heavy chain of a polypeptide sequence of SEQ ID NO: 60.

In one embodiment of the disclosure, when the mixture of two or more different anti-influenza virus antibodies (A) is a mixture of two different antibodies, the mixing ratio between the two different antibodies may be 9:1 to 1:9. In another embodiment of the disclosure, the mixing ratio may be 4:1 to 1:4. In still another embodiment of the disclosure, the mixing ratio may be 1:1. If the mixing ratio is within this range, the liquid pharmaceutical formulation may exhibit excellent stability. The mixing ratio may be freely controlled within a range that does not substantially adversely affect the stability of the stable liquid pharmaceutical formulation according to the disclosure.

In one embodiment of the disclosure, the concentration of the anti-influenza virus antibody or the mixture of two or more different anti-influenza virus antibodies may be 5 to 200 mg/mL. In another embodiment of the disclosure, the concentration may be 10 to 150 mg/mL. In still another embodiment of the disclosure, the concentration may be 20 to 100 mg/mL. If the concentration is within this range, the liquid pharmaceutical formulation may exhibit excellent long-term stability. The concentration may be freely controlled within a range that does not substantially adversely affect the stability of the stable liquid pharmaceutical formulation according to the disclosure.

(B) Surfactant

Examples of the surfactant that is used in this disclosure include, but are not limited to, polyoxyethylene sorbitan fatty acid ester (e.g., polysorbate), polyoxyethylene alkyl ether (e.g., Brij), alkylphenyl polyoxyethylene ether (e.g., Triton-X), polyoxyethylene-polyoxypropylene copolymers (e.g., Poloxamer, Pluronic), sodium dodecyl sulfate (SDS), and the like.

In one embodiment of the disclosure, the surfactant may comprise polysorbate, poloxamer, or a mixture thereof. In another embodiment of the disclosure, the surfactant may comprise polysorbate 20, polysorbate 40, polysorbate 60, polysorbate 80, or a mixture of two or more thereof. In another embodiment of the disclosure, the surfactant may comprise polysorbate 80.

In one embodiment of the disclosure, the concentration of the surfactant may be 0.001 to 10% (w/v). In another embodiment of the disclosure, the concentration of the surfactant may be 0.01 to 1.0% (w/v). In still another embodiment of the disclosure, the concentration of the surfactant may be 0.05 to 0.5% (w/v). If the concentration is within this range, the liquid pharmaceutical formulation may exhibit excellent stability. The concentration may be freely controlled within a range that does not substantially adversely affect the stability of the stable liquid pharmaceutical formulation according to the disclosure.

(C) Sugar or its Derivative

The "sugar" that is used in this disclosure may comprise a monosaccharide, a disaccharide, an oligosaccharide, a polysaccharide, or a mixture of two or more thereof. Examples of the monosaccharide include, but are not limited to, glucose, fructose, galactose, and the like. Examples of the disaccharide include, but are not limited to, sucrose, lactose, maltose, trehalose, and the like. Examples of the oligosaccharide include, but are not limited to, fructooligosaccharides, galactooligosaccharides, mannanoligosaccharides, and the like. Examples of the polysaccharide include, but are not limited to, starch, glycogen, cellulose, chitin, pectin, and the like.

The "sugar derivative" that is used in the disclosure may comprise sugar alcohol, sugar acid, or a mixture thereof. Examples of the sugar alcohol include, but are not limited to, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, and the like. Examples of the sugar acid include, but are not limited to, aldonic acid (glyceric acid, etc.), ulosonic acid (neuraminic acid, etc.), uronic acid (glucuronic acid, etc.), aldaric acid (tartaric acid, etc.), and the like.

In one embodiment of the disclosure, the sugar may comprise a monosaccharide, a disaccharide, an oligosaccharide, a polysaccharide, or a mixture of two or more thereof, and the sugar derivative may comprise sugar alcohol, sugar acid, or a mixture thereof. In one embodiment of the disclosure, the sugar or its derivative may comprise sorbitol, mannitol, trehalose, sucrose, or a mixture of two or more thereof.

In one embodiment of the disclosure, the concentration of the sugar or its derivative may be 0.01 to 30% (w/v). In another embodiment of the disclosure, the concentration may be 0.1 to 15% (w/v). In still another embodiment of the disclosure, the concentration may be 1.0 to 10% (w/v). If the concentration is within this range, the liquid pharmaceutical formulation may exhibit excellent stability. The concentration of the sugar or its derivative may be freely controlled within a range that does not substantially adversely affect the stability of the stable liquid pharmaceutical formulation according to the disclosure.

(D) Amino Acid

The "amino acid" that is used in the disclosure may comprise free amino acid, amino acid salt, or a mixture thereof. As used herein, the term "free amino acid" means a free-state amino acid in which there is no peptide bond between amino acid molecules or there is no ester bond between amino acid molecules and other molecules. Examples of the amino acid include, but are not limited to, aspartic acid, histidine, lysine, arginine, and the like. Examples of the amino acid salt include, but are not limited to, aspartic acid salt, histidine salt, lysine salt, arginine salt, and the like.

In one embodiment of the disclosure, the amino acid may comprise aspartic acid, histidine, lysine, arginine, or a salt thereof. In another embodiment of the disclosure, the amino acid may comprise histidine, histidine salt, or a mixture thereof.

In still another embodiment of the disclosure, the amino acid may comprise a mixture of histidine and histidine-HCl.

In one embodiment of the disclosure, the amino acid may comprise amino acid, amino acid salt, or a mixture thereof.

In still another embodiment of the disclosure, the amino acid may be a buffer.

The term "buffer" refers to a neutralizing substance that minimizes the change in pH caused by acid or alkali and that maintains pH in a specific range even in the absence of a pH-adjusting agent.

In one embodiment of the disclosure, the concentration of the amino acid may be 0.1 to 40 mM. In another embodiment of the disclosure, the concentration may be 1 to 20 mM. In still another embodiment of the disclosure, the concentration may be 5 to 15 mM. If the concentration is within this range, the liquid pharmaceutical formulation may exhibit excellent stability. The concentration of the amino acid may be freely controlled within a range that does not substantially adversely affect the stability of the stable liquid pharmaceutical formulation according to the disclosure.

(E) pH

The pH of the stable liquid pharmaceutical formulation according to the disclosure may be 5.5 to 6.5. If the pH is within this range, the liquid pharmaceutical formulation may exhibit excellent long-term stability. The pH of the liquid pharmaceutical formulation may be adjusted using the amino acid or the buffer. In other words, if the liquid pharmaceutical formulation contains a small amount of the amino acid or the buffer, it may exhibit the pH in the above-described range without having to use a separate pH-adjusting agent.

In another embodiment of the disclosure, the pH may be adjusted using an additional pH adjusting agent. Examples of the pH adjusting agent include, but are not limited to, acids, bases (e.g., sodium hydroxide), and the like.

(F) Other Components

The stable liquid pharmaceutical formulation of the disclosure may further comprise additives known in the art within a range that does not substantially adversely affect the activity of the antibody and the stability of the formulation.

In another embodiment of the disclosure, the additives may include, but are not limited to, an additional buffer, a diluent, a solubilizing agent, a pH adjusting agent, a sedative, other inorganic or organic salts, an antioxidant, an aqueous carrier, mixtures thereof, or the like. In still another embodiment of the disclosure, the liquid pharmaceutical formulation of the disclosure may further comprise aqueous carriers, antioxidants, or a mixture of two or more thereof. The aqueous carrier may comprise a carrier that is pharmaceutically acceptable (safe and non-toxic when administered to humans) and is useful for preparation of liquid pharmaceutical formulations.

(G) "Stable" Liquid Pharmaceutical Formulation

The term "stable" in the "stable liquid pharmaceutical formulation" of the disclosure means that the antibody according to the disclosure essentially retains its physical stability and/or chemical stability and/or biological activity during production and/or upon storage. Various analytical techniques for measuring antibody stability are readily available in the art.

In the disclosure, "physical stability" may be assessed by methods known in the art, which include measurement of a sample's apparent attenuation of light (absorbance, or optical density). Such a measurement of light attenuation is related to the turbidity of a formulation. In addition, for physical stability, the contents of high-molecular-weight components, the contents of low-molecular-weight components, the amounts of intact proteins, the number of sub-visible particles, and the like, may be measured.

In the present disclosure, "chemical stability" can be assessed by a method known in the art, and this method may comprise detecting and quantifying chemically altered forms of the antibody. In addition, for chemical stability, charge alteration (for example, occurring as a result of deamidation or oxidation) can be measured by, for example, ion-exchange chromatography. For chemical stability, charge variants (acidic or basic peaks) may be measured. The measurement of charge alteration by ion-exchange chromatography may be performed based on acidic or basic peaks.

As used herein, the term "storage stability" means that the antibody essentially retains its biological activity even in altered weather conditions, an elevated temperature and relative humidity environment, an environment in which shear stress acts, for example, during transport. The storage stability can be measured by various analytical techniques for measuring the biological activity of antibodies in an elevated temperature and relative humidity environment for a long period of time.

In the disclosure, biological activity may be assessed by methods known in the art. In such methods, antigen binding affinity may be measured by ELISA (Enzyme Linked Immuno Sorbent Assay).

In one embodiment of this disclosure, the liquid pharmaceutical formulation may be stable for a long period of time.

In one embodiment of this disclosure, the term "stable" liquid pharmaceutical formulation means a liquid pharmaceutical formulation satisfying one or more of the following criteria.

Appearance Analysis
- a liquid pharmaceutical formulation that retains its clear appearance after 6 weeks of storage at a temperature of 40±2° C. and a relative humidity of 75±5% under a closed condition;
- a liquid pharmaceutical formulation that retains its clear appearance after 12 months of storage at a temperature of 5±3° C. under a closed condition;

pH
- a liquid pharmaceutical formulation having a pH of 6.0±0.5 as measured after 12 months of storage at a temperature of 5±3° C. under a closed condition;

Sterile Condition
- a liquid pharmaceutical formulation that shows no microbial growth in medium in an isolator after 12 months of storage at a temperature of 5±3° C. under a closed condition;

Antibody Concentration
- a liquid pharmaceutical formulation in which the concentration of a single antibody is 50±5.0 mg/mL or the concentration of each of single antibodies constituting an antibody mixture is 25±2.5 mg/mL and the concentration of the antibody mixture is 50±5.0 mg/mL, as measured by HIC-HPLC after 6 weeks of storage at a temperature of 5±3° C. under a closed condition;
- a liquid pharmaceutical formulation in which the concentration of a single antibody is 50±5.0 mg/mL or the concentration of each of single antibodies constituting an antibody mixture is 25±2.5 mg/mL and the concentration of the antibody mixture is 50±5.0 mg/mL, as measured by HIC-HPLC after 6 weeks of storage at a temperature of 25±2° C. and a relative humidity of 60±5% under a closed condition;
- a liquid pharmaceutical formulation in which the concentration of a single antibody is 50±5.0 mg/mL or the concentration of each of single antibodies constituting an antibody mixture is 25±2.5 mg/mL and the concentration of the antibody mixture is 50±5.0 mg/mL, as measured by HIC-HPLC after 6 weeks of storage at a temperature of 40±2° C. and a relative humidity of 75±5% under a closed condition;
- a liquid pharmaceutical formulation in which the concentration of a single antibody is 50±5.0 mg/mL or the concentration of each of single antibodies constituting an antibody mixture is 25±2.5 mg/mL and the concentration of the antibody mixture is 50±5.0 mg/mL, as measured by HIC-HPLC after 12 months of storage at a temperature of 5±3° C. under a closed condition;

Content of Intact Immunoglobulin G (Intact IgG %)
- a liquid pharmaceutical formulation in which the content of intact immunoglobulin G (intact IgG %) is 95.0 to 100% as measured by chip-based CE-SDS after 6 weeks of storage at a temperature of 40±2° C. and a relative humidity of 75±5% under a closed condition;
- a liquid pharmaceutical formulation in which the content of intact immunoglobulin G (intact IgG %) is 90.0 to 100% as measured by non-reduced CE-SDS after 12 months of storage at a temperature of 5±3° C. under a closed condition;

Content of Intact Heavy Chain and Light Chain (Intact HC+LC %)
- a liquid pharmaceutical formulation in which the content of intact heavy chain and light chain (intact HC+LC %) is 95.0 to 100% as measured by reduced CE-SDS after 12 months of storage at a temperature of 5±3° C. under a closed condition;

Content of Antibody Monomers
- a liquid pharmaceutical formulation in which the content of antibody monomers is 95.0 to 100% as measured by SEC-HPLC after 6 weeks of storage at a temperature of 40±2° C. and a relative humidity of 75±5% under a closed condition;
- a liquid pharmaceutical formulation in which the content of antibody monomers is 95.0 to 100% as measured by SEC-HPLC after 12 months of storage at a temperature of 5±3° C. under a closed condition;

Influenza A Virus HA Binding Affinity
- a liquid pharmaceutical formulation having an HA binding affinity of 70 to 130% as measured by CELISA (Cellular Enzyme-Linked Immunosorbent Assay) or ELISA after 6 weeks of storage at a temperature of 5±3° C. under a closed condition;
- a liquid pharmaceutical formulation having an HA binding affinity of 70 to 130% as measured by CELISA (Cellular Enzyme-Linked Immunosorbent Assay) or ELISA after 6 weeks of storage at a temperature of 25±2° C. and a relative humidity of 60±5% under a closed condition;
- a liquid pharmaceutical formulation having an HA binding affinity of 70 to 130% as measured by CELISA (Cellular Enzyme-Linked Immunosorbent Assay) or ELISA after 6 weeks of storage at a temperature of 40±2° C. and a relative humidity of 75±5% under a closed condition; and
- a liquid pharmaceutical formulation having an HA binding affinity of 70 to 130% as measured by CELISA (Cellular Enzyme-Linked Immunosorbent Assay) or ELISA after 12 months of storage at a temperature of 5±3° C. under a closed condition.

Method for Preparation of Stable Liquid Pharmaceutical Formulation

The stable liquid pharmaceutical formulation of this disclosure may be prepared using any known method that is not limited to a particular method.

In one embodiment of the disclosure, the stable liquid pharmaceutical formulation may be prepared by a method comprising the steps of: i) adding an amino acid to a solution containing a sugar or its derivative to prepare a mixture solution; ii) exchanging buffer solution between the mixture solution of step i) with an antibody-containing solution to prepare an antibody-containing mixture solution; and iii) adding a surfactant to the antibody-containing mixture solution of step ii).

The term "buffer solution" refers to a substance that comprises a buffer and minimizes the change in pH caused by acid or alkali.

In one embodiment of the disclosure, a stable liquid pharmaceutical formulation comprising a mixture of two or more different anti-influenza virus antibodies may be prepared either by preparing stable liquid pharmaceutical formulations containing each antibody according to the above-described preparing method, and then mixing the prepared pharmaceutical formulations, or by preparing an antibody mixture, and then preparing a stable liquid pharmaceutical formulation using the prepared antibody mixture according to the above-described preparing method.

In one embodiment of the disclosure, the method for preparation of the formulation may comprise or not comprise a freeze-drying step.

In another embodiment of the disclosure, when the preparation method does not comprise the freeze-drying step, it may further comprise a step of treating the prepared liquid pharmaceutical formulation by sterilization or the like, and then immediately placing the liquid pharmaceutical formulation in a closed container.

In still another embodiment of the disclosure, when the preparation method comprises the freeze-drying step, the preparation method may further comprise a step of either freeze-drying or freeze-drying and storing the prepared liquid pharmaceutical formulation, and then supplementing or replacing components removed or modified by freeze drying and/or storage. Alternatively, the preparation method may comprise a step of either freeze-drying or freeze-drying and storing only components of the liquid pharmaceutical formulation of the disclosure, excluding components that may be removed or modified by freeze drying and/or storage, and then adding the excluded components.

Use of Stable Liquid Pharmaceutical Formulation

The stable liquid pharmaceutical formulation according to the disclosure may be used for diagnosis, prevention or treatment of influenza virus infection. In one embodiment of the disclosure, the stable liquid pharmaceutical formulation of the disclosure may be used for diagnosis, prevention or treatment of diseases caused by influenza virus infection. In another embodiment of the disclosure, diseases caused by influenza virus infection include, but are not limited to, pneumonia, otitis media, and the like.

In one embodiment of the present disclosure, the stable liquid pharmaceutical formulation may be administered intravenously, intramuscularly, transdermally, subcutaneously, intraperitoneally, topically, or a combination thereof.

In one embodiment of the disclosure, the stable liquid pharmaceutical formulation may be administered once or several times.

In one embodiment of the disclosure, the concentrations of other components, including the antibody, in the liquid pharmaceutical formulation, are as described above, and the total volume of the liquid pharmaceutical formulation may be 0.1 to 100 mL.

The dose and timing of administration of the liquid pharmaceutical formulation of the disclosure may vary depending on the kind of disease, the severity and course of the disease, the patient's health and response to treatment, and the judgment of the treating physician, and is not limited to a particular dose and timing of administration.

Method for Diagnosis, Prevention or Treatment

The disclosure also provides a method for diagnosis, prevention or treatment of influenza virus infection, the method comprising administering to a patient a stable liquid pharmaceutical formulation comprising: (A) an anti-influenza virus antibody or a mixture of two or more different anti-influenza virus antibodies; (B) a surfactant; (C) a sugar or its derivative; and (D) an amino acid.

In one embodiment of the disclosure, the method for prevention or treatment may comprise administering the pharmaceutical formulation together with a therapeutic agent known to those skilled in the art. In another embodiment of the disclosure, the method for prevention or treatment may further comprise administering an antiviral drug.

In still another embodiment of the disclosure, the antiviral drug may be an anti-influenza virus monoclonal antibody, an anti-influenza virus polyclonal antibody, a DNA polymerase inhibitor, a siRNA agent or a therapeutic vaccine, but is not limited thereto.

Method for Stabilization

This disclosure also provides a method of stabilizing an antibody in a liquid pharmaceutical formulation, the method comprising preparing a stable liquid pharmaceutical formulation comprising: (A) an anti-influenza virus antibody or a mixture of two or more different anti-influenza virus antibodies; (B) a surfactant; (C) a sugar or its derivative; and (D) an amino acid.

Kit

This disclosure also provides a kit comprising: a stable liquid pharmaceutical formulation comprising (A) an anti-influenza virus antibody or a mixture of two or more different anti-influenza virus antibodies, (B) a surfactant, (C) a sugar or its derivative, and (D) an amino acid; and a container receiving the stable liquid pharmaceutical formulation in a closed state.

In one embodiment of the disclosure, the container may be formed of a material such as glass, a polymer (plastic), a metal or the like, but is not limited thereto. In one embodiment of the disclosure, the container may be a bottle, a vial, a syringe, or a tube, but is not limited thereto.

In one embodiment of the disclosure, the container may be a glass or polymer vial, or a glass or polymer prefilled syringe.

In one embodiment of the disclosure, the inside of the container may not be coated with silicone oil. If it is coated with silicone oil, the stability of the formulation can be reduced. The container may be a single-dose container or a multiple-dose container.

Specific product forms of the above-described vial, cartridge, pre-filled syringe, auto-injector or the like, and methods of filling the stabile liquid pharmaceutical formulation into the vial, cartridge, pre-filled syringe, auto-injector or the like, may be readily available or implemented by any person skilled in the technical field to which the disclosure pertains. For example, U.S. Pat. Nos. 4,861,335 and 6,331,174, etc., disclose the specific product form of a pre-filled syringe and a method of filling into the pre-filled syringe. For example, U.S. Pat. Nos. 5,085,642 and 5,681,291, etc., disclose the specific product form of an auto-injector and an assembly method for the auto-injector. The above-described vial, cartridge, pre-filled syringe or auto-injector or the like, which is used in this disclosure, may be a commercially available product, or a product specifically manufactured considering the physical properties of the stable liquid pharmaceutical formulation, an area to which the formulation is to be administered, the dose of the formulation, and the like.

In one embodiment of the disclosure, the kit may further comprise instructions providing a method of using the stable liquid pharmaceutical formulation, a method of storing the formulation, or both. The method of using the formulation includes a method for diagnosis, prevention or treatment of influenza virus infection, and may include the route of administration, the dose of the formulation, and the timing of administration.

In one embodiment of the disclosure, the kit may comprise other tools necessary from a commercial viewpoint and a user viewpoint. In another embodiment of the disclosure, the other tools may include a needle, a syringe, and the like.

In one embodiment of the disclosure, the kit may further comprise a pharmaceutically acceptable excipient. The term "pharmaceutically acceptable excipient" means any inert substance that is combined with an active molecule (such as an antibody) for preparing an agreeable or convenient dosage form. The pharmaceutically acceptable excipient is an excipient that is non-toxic to recipients at the dosages and concentrations employed, and is compatible with other ingredients of the formulation comprising the monoclonal antibody.

Hereinafter, the disclosure will be described with reference to examples. It is to be understood, however, that these examples are for illustrative purposes only and are not intended to limit the scope of this disclosure. The documents cited in the disclosure, and Korean Patent Application Nos. 10-2011-0020061, 10-2012-0107512 and 10-2014-0036601, filed by the applicant, are incorporated herein by reference.

DETAILED DESCRIPTION

Examples

Identification, cloning, production and characterization of anti-influenza virus antibodies used in the following experimental examples are described in detail in Korean Patent Application Nos. 10-2011-0020061 and 10-2012-0107512, and mixtures of two or more different anti-influenza virus antibodies are described in detail in Korean Patent Application No. 10-2014-0036601.

In the following experimental examples, three of 11 antibodies selected in Example 4 of Korean Patent Application No. 10-2011-0020061, and four of 6 antibodies selected in Example 4 of Korean Patent Application No. 10-2012-0107512, hereinafter referred to as "antibody 1," "antibody 2," "antibody 3," "antibody 4," "antibody 5," "antibody 6," or "antibody 7," were used as anti-influenza virus antibodies. In addition, antibody mixtures comprising two or more of the above-described seven antibodies were used.

The physical stability, chemical stability and biological activity of liquid pharmaceutical formulations used in the following experimental examples were measured using the following methods.

The physical stability, chemical stability and biological activity measured by the following measurement methods may include measurement errors resulting from measurement environments and conditions.

Antibody Concentration

The concentration (mg/mL) of each of single antibodies and antibody mixtures was measured using HIC (Hydrophobic Interaction Chromatography)-HPLC.

Appearance Analysis

Based on the appearance of stored formulations, the clarity of the formulation solutions was measured.

pH Measurement

Using a pH meter, the pH of solutions was measured.

Sterility Test

The extent of microbial growth in a formulation solution in an isolator was measured.

Content of Intact Immunoglobulin G (Intact IgG %)

Using chip-based capillary electrophoresis-sodium dodecyl sulfate (CE-SDS) or non-reduced CE-SDS, the content of intact immunoglobulin G (intact IgG %) was measured.

Content of Intact Heavy Chain and Light Chain (Intact HC+LC %)

The content of intact heavy chain and light chain (intact HC+LC %) was measured using Reduced Capillary Electrophoresis-Sodium Dodecyl Sulfate (Reduced CE-SDS).

Influenza Virus Binding Affinity

Using enzyme-linked immunosorbent assay (ELISA) or cellular enzyme-linked immunosorbent assay (CELISA), influenza virus HA binding affinity (%) was measured.

Content of Antibody Monomers

Using size exclusion HPLC, the content of antibody monomers (main peak; %) was measured.

Experimental Example 1: Preparation of Formulations of Examples 1 to 9 and Comparative Examples 1 to 21

In order to select an optimized liquid pharmaceutical formulation comprising an anti-influenza virus antibody or a mixture of two or more different anti-influenza virus antibodies, candidate liquid pharmaceutical formulation components were applied to antibody 1 or antibody 2 as a single antibody or a 1:1 mixture of antibody 1 and antibody 2 as an antibody mixture in the following manner, thereby preparing formulations of Examples 1 to 9 and Comparative Examples 1 to 21.

Using each buffer, a buffer solution having a pH corresponding to optimal buffer capacity was prepared, and sugar, sugar alcohol or sodium chloride was added thereto. Then, to the solution containing buffer and sugar, sugar alcohol or sodium chloride, an anti-influenza virus antibody or a mixture of two or more different anti-influenza virus antibodies was added, and a surfactant was added to the solution so as to reach a desired concentration, thereby preparing candidate liquid pharmaceutical formulations.

The specific content of each component in the candidate liquid pharmaceutical formulation is shown in Table 1 below, and the total volume of the candidate liquid pharmaceutical formulation is 4 mL.

TABLE 1

| | Examples 1 to 9 and Comparative Examples 1 to 21 | | | | |
|---|---|---|---|---|---|
| | | | | Antibody concentration (mg/mL) | |
| | Buffer | pH | Sugar, sugar alcohol, or sodium chloride | Surfactant (w/v) | Antibody 1 | Antibody 2 |
| Example 1 | Histidine 10 mM | 6.0 | Sorbitol 5% (w/v) | Polysorbate 80 0.10% | 25 | 25 |
| Example 2 | Histidine 10 mM | 6.0 | Sorbitol 5% (w/v) | Polysorbate 80 0.10% | 50 | — |

TABLE 1-continued

Examples 1 to 9 and Comparative Examples 1 to 21

| | Buffer | pH | Sugar, sugar alcohol, or sodium chloride | Surfactant (w/v) | Antibody concentration (mg/mL) Antibody 1 | Antibody 2 |
|---|---|---|---|---|---|---|
| Example 3 | Histidine 10 mM | 6.0 | Sorbitol 5% (w/v) | Polysorbate 80 0.10% | — | 50 |
| Example 4 | Histidine 10 mM | 6.0 | Sorbitol 5% (w/v) | Polysorbate 80 0.05% | 25 | 25 |
| Example 5 | Histidine 10 mM | 6.0 | Sorbitol 5% (w/v) | Polysorbate 80 0.05% | 50 | — |
| Example 6 | Histidine 10 mM | 6.0 | Sorbitol 5% (w/v) | Polysorbate 80 0.05% | — | 50 |
| Example 7 | Histidine 10 mM | 6.0 | Sorbitol 5% (w/v) | Polysorbate 80 0.02% | 25 | 25 |
| Example 8 | Histidine 10 mM | 6.0 | Sorbitol 5% (w/v) | Polysorbate 80 0.02% | 50 | — |
| Example 9 | Histidine 10 mM | 6.0 | Sorbitol 5% (w/v) | Polysorbate 80 0.02% | — | 50 |
| Comparative Example 1 | Histidine 10 mM | 6.0 | Sodium chloride 140 mM | Polysorbate 80 0.05% | 25 | 25 |
| Comparative Example 2 | Histidine 10 mM | 6.0 | Sodium chloride 140 mM | Polysorbate 80 0.05% | 50 | — |
| Comparative Example 3 | Histidine 10 mM | 6.0 | Sodium chloride 140 mM | Polysorbate 80 0.05% | — | 50 |
| Comparative Example 4 | Sodium acetate 10 mM | 4.0 | Sodium chloride 140 mM | Polysorbate 80 0.05% | 25 | 25 |
| Comparative Example 5 | Sodium acetate 10 mM | 4.0 | Sodium chloride 140 mM | Polysorbate 80 0.05% | 50 | — |
| Comparative Example 6 | Sodium acetate 10 mM | 4.0 | Sodium chloride 140 mM | Polysorbate 80 0.05% | — | 50 |
| Comparative Example 7 | Sodium acetate 10 mM | 4.0 | Sorbitol 5% (w/v) | Polysorbate 80 0.05% | 25 | 25 |
| Comparative Example 8 | Sodium acetate 10 mM | 4.0 | Sorbitol 5% (w/v) | Polysorbate 80 0.05% | 50 | — |
| Comparative Example 9 | Sodium acetate 10 mM | 4.0 | Sorbitol 5% (w/v) | Polysorbate 80 0.05% | — | 50 |
| Comparative Example 10 | Sodium acetate 10 mM | 5.0 | Sodium chloride 140 mM | Polysorbate 80 0.05% | 25 | 25 |
| Comparative Example 11 | Sodium acetate 10 mM | 5.0 | Sodium chloride 140 mM | Polysorbate 80 0.05% | 50 | — |
| Comparative Example 12 | Sodium acetate 10 mM | 5.0 | Sodium chloride 140 mM | Polysorbate 80 0.05% | — | 50 |
| Comparative Example 13 | Sodium acetate 10 mM | 5.0 | Sorbitol 5% (w/v) | Polysorbate 80 0.05% | 25 | 25 |
| Comparative Example 14 | Sodium acetate 10 mM | 5.0 | Sorbitol 5% (w/v) | Polysorbate 80 0.05% | 50 | — |
| Comparative Example 15 | Sodium acetate 10 mM | 5.0 | Sorbitol 5% (w/v) | Polysorbate 80 0.05% | — | 50 |
| Comparative Example 16 | Sodium phosphate 10 mM | 6.0 | Sodium chloride 140 mM | Polysorbate 80 0.05% | 25 | 25 |
| Comparative Example 17 | Sodium phosphate 10 mM | 6.0 | Sodium chloride 140 mM | Polysorbate 80 0.05% | 50 | — |
| Comparative Example 18 | Sodium phosphate 10 mM | 6.0 | Sodium chloride 140 mM | Polysorbate 80 0.05% | — | 50 |
| Comparative Example 19 | Sodium phosphate 10 mM | 6.0 | Sorbitol 5% (w/v) | Polysorbate 80 0.05% | 25 | 25 |

TABLE 1-continued

Examples 1 to 9 and Comparative Examples 1 to 21

| | Buffer | Sugar, sugar alcohol, or sodium pH chloride | | Surfactant (w/v) | Antibody concentration (mg/mL) | |
|---|---|---|---|---|---|---|
| | | | | | Antibody 1 | Antibody 2 |
| Comparative Example 20 | Sodium phosphate 10 mM | 6.0 | Sorbitol 5% (w/v) | Polysorbate 80 0.05% | 50 | — |
| Comparative Example 21 | Sodium phosphate 10 mM | 6.0 | Sorbitol 5% (w/v) | Polysorbate 80 0.05% | — | 50 |

Experimental Example 2: Comparison of Stability Between Examples 1 to 9 and Comparative Examples 1 to 21

The formulations of Examples 1 to 9 and Comparative Examples 1 to 21 were stored at 5±3° C., 25±2° C./60±5% relative humidity, and 40±2° C./75±5% relative humidity. After 2 weeks, 4 weeks and 6 weeks of storage under each of the above-described temperatures and relative humidity conditions, the stability of each formulation was measured.

To compare stability between the formulations of Examples 1 to 9 and Comparative Examples 1 to 21, appearance analysis, antibody concentration measurement, measurement of the content of intact immunoglobulin G, measurement of the content of antibody monomers, and measurement of binding affinity (ELISA and CELISA) were performed.

The formulations of the Examples and the Comparative Examples, which comprise antibody 1 or antibody 2 as a single antibody, showed the same tendency as that of the formulations of the Examples and the Comparative Examples, which comprise the mixture of antibody 1 and antibody 2. Thus, the results of measuring the stabilities of the formulations of representative Examples 1, 4 and 7 and Comparative Examples 1, 4, 7, 10, 13, 16 and 19, which comprise the antibody mixture, are described in the specification.

(1) Appearance Analysis

For the formulations of Examples 1, 4 and 7 and Comparative Examples 1, 4, 7, 10, 13, 16 and 19, appearance analysis was performed to determine visually observed particles and clarity. Evaluation was performed according to the following criteria: clear=a formulation that is not turbid; very slightly opalescent=a formulation that does not apparently shows visible particles, but is turbid; slightly opalescent=a formulation that does not apparently show visible particles, but is very turbid; opalescent=a formulation that shows a form like gelatin.

As can be seen in Table 2 below, at 40±2° C./75±5% relative humidity, the formulation of Comparative Example 4, which comprises acetate buffer (pH 4.0) and 140 mM sodium chloride, was gelatinized after 4 weeks so that it could not be analyzed (inaccessible state (IS)). Under all temperature conditions, the formulations of Examples 1, 4 and 7 and Comparative Examples 1, 7, 10, 13, 16 and 19 did not show the presence of visible particles for 6 weeks, but the formulations of Comparative Examples 1, 4, 10 and 16, which comprise sodium chloride, showed a very slightly opalescent appearance or a slightly opalescent appearance, whereas the formulations of Examples 1, 4 and 7, and Comparative Examples 7, 13 and 19, which comprise sorbitol, showed a clear appearance.

Thus, under all the temperature conditions, the formulations comprising sorbitol rather than sodium chloride maintained their clear appearance.

In a subsequent experiment, analysis was performed on the formulations of Examples 1, 4 and 7 and Comparative Examples 1, 7, 10, 13, 16 and 19, excluding the formulation of Comparative Example 4, which was gelatinized.

TABLE 2

| | Temperature | 0 week | After 2 weeks | After 4 weeks | After 6 weeks |
|---|---|---|---|---|---|
| Example 1 | 5 ± 3° C. | Clear | Clear | Clear | Clear |
| | 25 ± 2° C./60 ± 5% relative humidity | Clear | Clear | Clear | Clear |
| | 40 ± 2° C./75 ± 5% relative humidity | Clear | Clear | Clear | Clear |
| Example 4 | 5 ± 3° C. | Clear | Clear | Clear | Clear |
| | 25 ± 2° C./60 ± 5% relative humidity | Clear | Clear | Clear | Clear |
| | 40 ± 2° C./75 ± 5% relative humidity | Clear | Clear | Clear | Clear |
| Example 7 | 5 ± 3° C. | Clear | Clear | Clear | Clear |
| | 25 ± 2° C./60 ± 5% relative humidity | Clear | Clear | Clear | Clear |
| | 40 ± 2° C./75 ± 5% relative humidity | Clear | Clear | Clear | Clear |
| Comparative Example 1 | 5 ± 3° C. | Very slightly opalescent | Very slightly opalescent | Very slightly opalescent | Very slightly opalescent |
| | 25 ± 2° C./60 ± 5% relative humidity | Very slightly opalescent | Very slightly opalescent | Very slightly opalescent | Very slightly opalescent |

TABLE 2-continued

|  | Temperature | 0 week | After 2 weeks | After 4 weeks | After 6 weeks |
|---|---|---|---|---|---|
| | 40 ± 2° C./75 ± 5% relative humidity | Very slightly opalescent | Very slightly opalescent | Very slightly opalescent | Very slightly opalescent |
| Comparative Example 4 | 5 ± 3° C. | Very slightly opalescent | Very slightly opalescent | Very slightly opalescent | Very slightly opalescent |
| | 25 ± 2° C./60 ± 5% relative humidity | Very slightly opalescent | Very slightly opalescent | Very slightly opalescent | Very slightly opalescent |
| | 40 ± 2° C./75 ± 5% relative humidity | Very slightly opalescent | Slightly opalescent | Opalescent | Opalescent |
| Comparative Example 7 | 5 ± 3° C. | Clear | Clear | Clear | Clear |
| | 25 ± 2° C./60 ± 5% relative humidity | Clear | Clear | Clear | Clear |
| | 40 ± 2° C./75 ± 5% relative humidity | Clear | Clear | Clear | Clear |
| Comparative Example 10 | 5 ± 3° C. | Very slightly opalescent | Very slightly opalescent | Very slightly opalescent | Very slightly opalescent |
| | 25 ± 2° C./60 ± 5% relative humidity | Very slightly opalescent | Very slightly opalescent | Very slightly opalescent | Very slightly opalescent |
| | 40 ± 2° C./75 ± 5% relative humidity | Very slightly opalescent | Very slightly opalescent | Very slightly opalescent | Very slightly opalescent |
| Comparative Example 13 | 5 ± 3° C. | Clear | Clear | Clear | Clear |
| | 25 ± 2° C./60 ± 5% relative humidity | Clear | Clear | Clear | Clear |
| | 40 ± 2° C./75 ± 5% relative humidity | Clear | Clear | Clear | Clear |
| Comparative Example 16 | 5 ± 3° C. | Very slightly opalescent | Very slightly opalescent | Very slightly opalescent | Very slightly opalescent |
| | 25 ± 2° C./60 ± 5% relative humidity | Very slightly opalescent | Very slightly opalescent | Very slightly opalescent | Very slightly opalescent |
| | 40 ± 2° C./75 ± 5% relative humidity | Very slightly opalescent | Very slightly opalescent | Very slightly opalescent | Very slightly opalescent |
| Comparative Example 19 | 5 ± 3° C. | Clear | Clear | Clear | Clear |
| | 25 ± 2° C./60 ± 5% relative humidity | Clear | Clear | Clear | Clear |
| | 40 ± 2° C./75 ± 5% relative humidity | Clear | Clear | Clear | Clear |

(2) Antibody Concentration

For the formulations of Examples 1, 4 and 7 and Comparative Examples 1, 7, 10, 13, 16 and 19, the concentration of each of antibody 1 and antibody 2 in the antibody mixture was measured by HIC (Hydrophobic Interaction Chromatography)-HPLC.

As a result, it could be seen that there was no change under all the temperature conditions (data not shown).

(3) Content (%) of Intact Immunoglobulin G

For the formulations of Examples 1, 4 and 7 and Comparative Examples 1, 7, 10, 13, 16 and 19, the content of intact immunoglobulin G was measured using Labchip GXII that is a chip-based CE-SDS analysis system.

As can be seen in Table 3 below, after 6 weeks at 40±2° C./75±5% relative humidity, the formulations of Examples 1, 4 and 7 and Comparative Example 1, which comprise histidine buffer, and the formulations of Comparative Examples 16 and 19, which comprise phosphate buffer, showed a purity of 95% or higher, whereas the formulations of Comparative Examples 7 and 10, which comprise acetate buffer, showed a purity lower than 95%.

Thus, it could be seen that, under the high-temperature condition, the formulations comprising histidine buffer or phosphate buffer rather than acetate buffer maintained an intact immunoglobulin G content of 95% or more as measured by CE-SDS, and thus were stable against degradation. As used herein, the term "degradation" means that the characteristics of protein are changed at a temperature (40±2° C. in this disclosure) higher than the temperature of the human body.

TABLE 3

| | Temperature | 0 week | After 2 weeks | After 4 weeks | After 6 weeks |
|---|---|---|---|---|---|
| Example 1 | 5 ± 3° C. | 98.42 | 98.57 | 98.35 | 98.00 |
| | 25 ± 2° C./60 ± 5% relative humidity | 98.42 | 98.61 | 98.47 | 97.90 |
| | 40 ± 2° C./75 ± 5% relative humidity | 98.42 | 98.32 | 96.54 | 96.40 |
| Example 4 | 5 ± 3° C. | 98.44 | 98.69 | 98.35 | 98.48 |
| | 25 ± 2° C./60 ± 5% relative humidity | 98.44 | 98.53 | 98.47 | 97.80 |
| | 40 ± 2° C./75 ± 5% relative humidity | 98.44 | 98.26 | 96.62 | 96.42 |
| Example 7 | 5 ± 3° C. | 98.46 | 98.59 | 98.39 | 98.33 |
| | 25 ± 2° C./60 ± 5% relative humidity | 98.46 | 98.58 | 98.51 | 98.03 |
| | 40 ± 2° C./75 ± 5% relative humidity | 98.46 | 98.28 | 96.69 | 96.34 |
| Comparative Example 1 | 5 ± 3° C. | 98.38 | 98.67 | 98.35 | 98.61 |
| | 25 ± 2° C./60 ± 5% relative humidity | 98.38 | 98.61 | 98.47 | 97.81 |
| | 40 ± 2° C./75 ± 5% relative humidity | 98.38 | 98.22 | 96.35 | 96.28 |
| Comparative Example 7 | 5 ± 3° C. | 98.47 | 98.55 | 98.32 | 98.51 |
| | 25 ± 2° C./60 ± 5% relative humidity | 98.47 | 98.54 | 98.44 | 97.47 |
| | 40 ± 2° C./75 ± 5% relative humidity | 98.47 | 98.16 | 95.58 | 94.52 |
| Comparative Example 10 | 5 ± 3° C. | 98.36 | 98.65 | 98.31 | 98.34 |
| | 25 ± 2° C./60 ± 5% relative humidity | 98.36 | 98.45 | 98.43 | 97.17 |
| | 40 ± 2° C./75 ± 5% relative humidity | 98.36 | 97.85 | 93.49 | 91.95 |
| Comparative Example 13 | 5 ± 3° C. | 98.43 | 98.68 | 98.31 | 98.47 |
| | 25 ± 2° C./60 ± 5% relative humidity | 98.43 | 98.47 | 98.43 | 97.73 |

TABLE 3-continued

|  | Temperature | 0 week | After 2 weeks | After 4 weeks | After 6 weeks |
|---|---|---|---|---|---|
|  | 40 ± 2° C./75 ± 5% relative humidity | 98.43 | 98.18 | 96.19 | 95.07 |
| Comparative Example 16 | 5 ± 3° C. | 98.48 | 98.56 | 98.33 | 97.98 |
|  | 25 ± 2° C./60 ± 5% relative humidity | 98.48 | 98.64 | 98.45 | 97.17 |
|  | 40 ± 2° C./75 ± 5% relative humidity | 98.48 | 98.20 | 95.61 | 96.26 |
| Comparative Example 19 | 5 ± 3° C. | 98.46 | 98.62 | 98.38 | 98.27 |
|  | 25 ± 2° C./60 ± 5% relative humidity | 98.46 | 98.59 | 98.50 | 97.70 |
|  | 40 ± 2° C./75 ± 5% relative humidity | 98.46 | 98.21 | 96.40 | 95.77 |

(4) Content of Antibody Monomers (%)

For the formulations of Examples 1, 4 and 7 and Comparative Examples 1, 7, 10, 13, 16 and 19, the content of antibody monomers was measured using SEC-HPLC.

As a result, as can be seen in Table 4 below, after 6 weeks at 40±2° C./75±5% relative humidity, the formulations of Examples 1, 4 and 7, which comprise histidine buffer (pH 6.0) and 5% sorbitol, showed a purity of 95% or higher, whereas the formulations of Comparative Examples 1, 7, 10, 13, 16 and 19, which comprise acetate buffer or phosphate buffer, showed a purity lower than 95%. In addition, it could be seen that, in the formulation of Comparative Example 7, which comprises acetate buffer (pH 4.0), the ratio of fragments appearing later than the main peak on the chromatogram was relatively high, and in the formulations of Comparative Examples 16 and 17, which comprises phosphate buffer, the ratio of aggregates appearing earlier than the main peak on the chromatogram was relatively high (data not shown).

Thus, it could be seen that, under the high-temperature condition, the formulation comprising histidine buffer rather than acetate buffer or phosphate buffer maintained an antibody monomer content of 95% or higher as measured by SEC-HPLC, and thus was stable against degradation. Furthermore, it could be seen that the formulations of Comparative Examples 1, 10 and 16, which comprise sodium chloride, showed monomer contents lower than those of the formulations of Examples 1, 4 and 7 and Comparative Examples 1, 7, 13 and 19, which comprise sodium chloride, indicating that sorbitol is more stable against deterioration than sodium chloride.

TABLE 4

|  | Temperature | 0 week | After 2 weeks | After 4 weeks | After 6 weeks |
|---|---|---|---|---|---|
| Example 1 | 5 ± 3° C. | 99.17 | 99.12 | 99.23 | 99.10 |
|  | 25 ± 2° C./60 ± 5% relative humidity | 99.17 | 99.08 | 99.23 | 98.80 |
|  | 40 ± 2° C./75 ± 5% relative humidity | 99.17 | 96.91 | 96.12 | 95.69 |
| Example 4 | 5 ± 3° C. | 99.20 | 99.15 | 99.23 | 99.12 |
|  | 25 ± 2° C./60 ± 5% relative humidity | 99.20 | 99.11 | 99.05 | 98.91 |
|  | 40 ± 2° C./75 ± 5% relative humidity | 99.20 | 96.96 | 96.33 | 95.83 |
| Example 7 | 5 ± 3° C. | 99.20 | 99.17 | 99.27 | 99.17 |
|  | 25 ± 2° C./60 ± 5% relative humidity | 99.20 | 99.11 | 99.08 | 98.92 |
|  | 40 ± 2° C./75 ± 5% relative humidity | 99.20 | 97.17 | 96.05 | 95.78 |
| Comparative Example 1 | 5 ± 3° C. | 99.13 | 99.04 | 99.14 | 98.99 |
|  | 25 ± 2° C./60 ± 5% relative humidity | 99.13 | 98.98 | 98.80 | 98.62 |
|  | 40 ± 2° C./75 ± 5% relative humidity | 99.13 | 96.62 | 95.28 | 94.67 |
| Comparative Example 7 | 5 ± 3° C. | 99.41 | 99.35 | 99.43 | 99.33 |
|  | 25 ± 2° C./60 ± 5% relative humidity | 99.41 | 99.32 | 99.31 | 99.16 |
|  | 40 ± 2° C./75 ± 5% relative humidity | 99.41 | 97.21 | 95.46 | 94.73 |
| Comparative Example 10 | 5 ± 3° C. | 99.17 | 99.15 | 99.22 | 99.04 |
|  | 25 ± 2° C./60 ± 5% relative humidity | 99.17 | 98.96 | 98.77 | 98.58 |
|  | 40 ± 2° C./75 ± 5% relative humidity | 99.17 | 96.03 | 93.59 | 91.46 |
| Comparative Example 13 | 5 ± 3° C. | 99.34 | 99.39 | 99.41 | 99.29 |
|  | 25 ± 2° C./60 ± 5% relative humidity | 99.34 | 99.28 | 99.27 | 99.04 |
|  | 40 ± 2° C./75 ± 5% relative humidity | 99.34 | 97.11 | 96.13 | 95.57 |
| Comparative Example 16 | 5 ± 3° C. | 98.78 | 98.79 | 98.85 | 98.77 |
|  | 25 ± 2° C./60 ± 5% relative humidity | 98.78 | 98.60 | 98.43 | 98.29 |
|  | 40 ± 2° C./75 ± 5% relative humidity | 98.78 | 96.08 | 94.77 | 94.20 |
| Comparative Example 19 | 5 ± 3° C. | 98.92 | 98.91 | 99.01 | 98.83 |
|  | 25 ± 2° C./60 ± 5% relative humidity | 98.92 | 98.86 | 98.72 | 98.50 |
|  | 40 ± 2° C./75 ± 5% relative humidity | 98.92 | 96.51 | 95.41 | 94.71 |

(5) Measurement of Binding Affinity

For the formulations of Examples 1, 4 and 7 and Comparative Examples 1, 7, 10, 13, 16 and 19, antibody binding affinity was measured using ELISA and CELISA.

Using CHO cells expressing H1(H1N1) or H3(H3N2) subtype HA, the binding affinity of each of antibody 1 and antibody 2 was measured by CELISA, and the binding affinities of a mixture of antibody 1 and antibody 2 for H5(H5N1) subtype HA were measured by ELISA.

As a result, it could be seen that, under all the temperature conditions, the binding affinity for HA was 70 to 130% (data not shown).

Experimental Example 3: Additional Experiment on the Kind and Concentration of Formulation Components (1) Antibody As confirmed in Examples 1, 4 and 7 of Experimental Example 2, the formulation comprising the mixture of antibody 1 and antibody 2 was stable. In antibody concentration measurement, measurement of the content of intact immunoglobulin G, measurement of the content of antibody monomers and measurement of binding affinity (ELISA and CELISA) in Experimental Example 2, the stability of each of antibody 1 and antibody 2 was evaluated. As a result, it was shown that the stability of antibody 1 or antibody 2, which is a single antibody, showed the same tendency as that of the antibody mixture.

Additionally, the concentration of the antibody mixture in the formulation of Example 1 was changed to 150 mg/ml, and appearance analysis, antibody concentration measurement, etc., were performed. As a result, it was shown that the formulation was stable (data not shown).

(2) Surfactant

As confirmed in Examples 1, 4 and 7 of Experimental Example 2, the formulations comprising the surfactant were stable. In order to examine whether the formulations are also stable even when they comprise other surfactants, the surfactant in the formulations of Examples 1, 4 and 7 was replaced with polysorbate 20 or poloxamer 188, and after 6 weeks, the appearance of the formulations was analyzed. As a result, the formulations were all stable (data not shown).

Additionally, the concentration of polysorbate 80 in the formulation of Example 1 was changed to 0.01% and 1.0%, and appearance analysis, antibody concentration measurement, etc., were performed. As a result, it was shown that the formulation was stable (data not shown).

(3) Sugar or its Derivative

As confirmed in Examples 1, 4 and 7 of Experimental Example 2, the formulations comprising the sugar or its derivative were stable. In order to examine whether the formulations are also stable even when they comprise other sugars or their derivatives, sorbitol in the formulations of Examples 1, 4 and 7 was replaced with mannitol, trehalose or sucrose, and after 6 weeks, the appearance of the formulations was analyzed. As a result, the formulations were all stable (data not shown).

Additionally, the concentration of sorbitol in the formulation of Example 1 was changed to 0.1% and 15%, and appearance analysis, antibody concentration measurement, etc., were performed. As a result, it was shown that the formulation was stable (data not shown).

(4) Amino Acid

As confirmed in Examples 1, 4 and 7 of Experimental Example 2, the formulations comprising the amino acid were stable. In order to examine whether the formulations are also stable even when they comprise other amino acids or amino acid salts, aspartic acid, lysine or arginine was added to the formulations of Examples 1, 4 and 7, and after 6 weeks, the appearance of the formulations was analyzed. As a result, the formulations were all stable (data not shown). Furthermore, histidine in the formulations of Examples 1, 4 and 7 was replaced with histidine-HCl, and after 6 weeks, the appearance of the formulations was analyzed. As a result, the formulations were all stable (data not shown).

Additionally, the concentration of histidine in the formulation of Example 1 was changed to 1 mM and 20 mM, and appearance analysis, antibody concentration measurement, etc., were performed. As a result, it was shown that the formulation was stable (data not shown).

Experimental Example 4: Determination of Stable Liquid Pharmaceutical Formulation (1) Analysis of the Results of Experimental Examples 2 and 3

The results of comparison of appearance analysis suggested that the formulation comprising sorbitol is more stable than the formulation comprising sodium chloride. The results of comparison of the intact antibody content suggested that the formulation comprising histidine buffer or phosphate buffer is more stable against degradation than the formulation comprising acetate buffer. The results of comparison of the monomer content suggested that the formulation comprising histidine buffer is more stable against degradation than the formulation comprising acetate buffer or phosphate buffer. The results of all the analytical experiments suggested that the formulation stability did not change depending on the concentration of polysorbate 80, which is surfactant.

(2) Sub-Conclusion

Not only in appearance analysis, but also in antibody concentration measurement, measurement of the content of intact immunoglobulin G, measurement of the content of antibody monomers and measurement of binding affinity (ELISA and CELISA) in Experimental Example 2, it was shown that the formulations of Examples 1, 4 and 7 were all stable. Such formulations comprising histidine buffer and sorbitol for the single anti-influenza antibody or the mixture of two or more different anti-influenza antibodies were shown to be stable liquid pharmaceutical formulations.

A surfactant in a liquid pharmaceutical formulation functions to inhibit surface adsorption or antibody aggregation. However, generally, the surfactant itself that is a polymer may have a tendency to be degraded so as to reduce its content, as the storage time increases. Thus, considering the degradation rate of the surfactant, it is required that the surfactant should be used at a high concentration so that its function as an inhibitor against surface adsorption and antibody aggregation will be maintained for a long period of time. Accordingly, among the candidate liquid pharmaceutical formulations, the formulation having the highest surfactant content (0.1%) was determined to be optimal (data not shown).

Thus, the formulation of Example 1, which comprises 10 mM histidine (pH 6.0), 5% sorbitol and 0.1% polysorbate 80, was tested for long-term stability.

Experimental Example 5: Application of Stable Liquid Pharmaceutical Formulation to Other Anti-Influenza Single Antibody and Antibody Mixtures The components of the stable liquid pharmaceutical formulations of Example 1 were applied to antibodies 3 to 7 and mixtures thereof, and stored at 5±3° C., 25±2° C./60±5% relative humidity and 40±2° C./75±5% relative humidity in the same manner as Experimental Example 2. After 2 weeks, 4 weeks and 6 weeks under each of the temperature and humidity conditions, the stabilities of the formulations were analyzed. As a result, it was shown that the stabilities of all the single antibodies and the antibody mixtures were maintained, like that of Example 1 (data not shown).

Experimental Example 6: Evaluation of Long-Term Stability of Formulation of Example 1

Long-term stability evaluation of the formulation of Example 1 was performed according to a guideline (Guideline Q5C Quality of Biotechnological Products: Stability Testing of Biotechnological or Biological Products and ICH Guideline Q1A (R2): Stability Testing of New Drug Substances and Drug Products) provided in International Conference on Harmonisation (ICH).

50 mL of the stable liquid pharmaceutical formulation of Example 1, prepared according to the method of Experimental Example 1, was stored in a closed container at 5±3° C. At this temperature, the stability of the formulation was measured for 12 months.

To evaluate the long-term stability of the formulation of Example 1, appearance analysis, pH measurement, sterility test, antibody concentration measurement, measurement of intact immunoglobulin G content by non-reduced CE-SDS, measurement of intact heavy chain and light chain content by reduced CE-SDS, measurement of antibody monomer content, and measurement of binding affinity (H5N1 ELISA, H1N1 CELISA, and H3N2 CELISA) were performed. The results are shown in Tables 5 to 14 below.

(1) Appearance Analysis

TABLE 5

|  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- |
| Example 1 | Clear | Clear | Clear | Clear | Clear |

As shown in Table 5 above, the formulation of Example 1 maintained its clear appearance without changes in appearance for 12 months at 5±3° C., indicating that it is stable.

(2) pH Measurement

TABLE 6

|  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- |
| Example 1 | 6.1 | 6.1 | 6.1 | 6.1 | 6.1 |

As shown in Table 6 above, the formulation of Example 1 maintained its pH without changes for 12 months at 5±3° C., indicating that it is stable.

(3) Sterility Test

TABLE 7

|  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- |
| Example 1 | No bacterial growth | Not analyzed | No bacterial growth | No bacterial growth | No bacterial growth |

As shown in Table 7 above, the formulation of Example 1 maintained a sterile condition for 12 months at 5±3° C., indicating that it is stable.

(4) Antibody Concentration (Mg/mL)

TABLE 8

|  |  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- | --- |
| Example 1 | Antibody 1 (mg/mL) | 24.0 | 23.5 | 24.4 | 23.5 | 23.8 |
|  | Antibody 2 (mg/mL) | 25.1 | 25.2 | 25.8 | 24.7 | 25.1 |
|  | Antibody 1 + antibody 2 (mg/mL) | 49.0 | 48.7 | 50.2 | 48.2 | 48.9 |

As can be seen in Table 8 above, the formulation of Example 1 retained its antibody concentration without changes for 12 months at 5±3° C., indicating that it is stable.

(5) Content of Intact Immunoglobulin G (Intact IgG %)

TABLE 9

|  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- |
| Example 1 | 94.6 | 96.7 | 97.4 | 97.1 | 97.1 |

As shown in Table 9 above, the formulation of Example 1 showed a high intact immunoglobulin G content of 97% or more after 12 months at 5±3° C., indicating that it is stable.

(6) Content of Intact Heavy-Chain and Light-Chain (Intact HC+LC %)

TABLE 10

|  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- |
| Example 1 | 98.6 | 98.5 | 98.5 | 98.4 | 98.7 |

As shown in Table 10 above, the formulation of Example 1 showed a high intact heavy-chain and light-chain content of 98% or more after 12 months at 5±3° C., indicating that it is stable.

(7) Antibody Monomer Content (%)

TABLE 11

|  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- |
| Example 1 | 99.3 | 99.0 | 99.0 | 98.9 | 98.8 |

As shown in Table 11 above, the formulation of Example 1 showed a high antibody monomer content of 98% or more after 12 months at 5±3° C., indicating that it is stable.

(8) Binding Affinity (%)

The results of H5N1 ELISA, H1N1 CELISA and H3N2 CELISA are shown in Tables 12 and 13 below.

TABLE 12

Binding affinity for influenza A virus HA (H5N1)

|  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- |
| Example 1 | 95 | 106 | 99 | 105 | 106 |

As can be seen in Table 12, the formulation of Example 1 showed a binding affinity of 70 to 130% for influenza A virus HA H5N1 subtype after 12 months at 5±3° C., indicating that it is stable.

TABLE 13

Binding affinity (%) for influenza A virus HA (H1N1)

|  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- |
| Example 1 | 97 | 107 | 113 | 103 | 98 |

As can be seen in Table 13, the formulation of Example 1 showed a binding affinity of 70 to 130% for influenza A virus HA H1N1 subtype after 12 months at 5±3° C., indicating that it is stable.

TABLE 14

Binding affinity (%) for influenza A virus HA (H3N2)

|  | After 0 month at 5 ± 3° C. | After 3 months at 5 ± 3° C. | After 6 months at 5 ± 3° C. | After 9 months at 5 ± 3° C. | After 12 months at 5 ± 3° C. |
| --- | --- | --- | --- | --- | --- |
| Example 1 | 101 | 115 | 100 | 98 | 106 |

As can be seen in Table 14, the formulation of Example 1 showed a binding affinity of 70 to 130% for influenza A virus HA H3N2 subtype after 12 months at 5±3° C., indicating that it is stable.

Based on the above-described stability evaluation results, long-term stability data after 24 months will be evaluated.

The invention claimed is:

1. A stable liquid pharmaceutical formulation comprising:
   25 to 50 mg/mL of a mixture of two or more different anti-influenza virus (A) antibodies;
   (B) 0.02 to 0.1% (w/v) of a surfactant, wherein the surfactant (B) comprises polysorbate 80;
   (C) 1.0 to 5% (w/v) of a sugar or its derivative, wherein the sugar is sorbitol; and
   (D) 5 to 15 mM of histidine;
   wherein the pharmaceutical formulation has a pH of 6, and
   wherein the mixture of two or more different anti-influenza virus antibodies (A) comprises:
   i) an antibody comprising a light-chain variable region comprising a CDR1 region of SEQ ID NO: 1, a CDR2 region of SEQ ID NO: 2 and a CDR3 region of SEQ ID NO: 3, and a heavy-chain variable region comprising a CDR1 region of SEQ ID NO: 4, a CDR2 region of SEQ ID NO: 5, and a CDR3 region of SEQ ID NO: 6; and
   ii) an antibody comprising a light-chain variable region comprising a CDR1 region of SEQ ID NO: 7, a CDR2 region of SEQ ID NO: 8 and a CDR3 region of SEQ ID NO: 9, and a heavy-chain variable region comprising a CDR1 region of SEQ ID NO: 10, a CDR2 region of SEQ ID NO: 11, and a CDR3 region of SEQ ID NO: 12.

2. The stable liquid pharmaceutical formulation of claim 1, wherein the anti-influenza virus antibody (A) binds to an epitope in a hemagglutinin (HA) protein of influenza A virus, in which the epitope comprises an amino acid residue at position 318 of an HA1 polypeptide and comprises amino acid residues at positions 41, 42, 45, 48, 49, 52 and 53 of an HA2 polypeptide.

3. The stable liquid pharmaceutical formulation of claim 1, wherein the mixture of two or more different anti-influenza virus antibodies (A) is a mixture of two different antibodies, and the ratio of the two different antibodies is 9:1 to 1:9.

4. The stable liquid pharmaceutical formulation of claim 1, which has an antibody monomer purity of 95% or higher as measured after 6 weeks of storage at 40±2° C.

5. The stable liquid pharmaceutical formulation of claim 1, which has an antibody monomer purity of 95% or higher as measured after 12 months of storage at 5±3° C.

6. The stable liquid pharmaceutical formulation of claim 1, which is configured for administration intravenously, intramuscularly, transdermally, subcutaneously, intraperitoneally, topically, or a combination thereof.

7. A pre-filled syringe filled with the stable liquid pharmaceutical formulation as set forth in claim 1.

8. An auto-injector including the pre-filled syringe of claim 7 therein.

9. A kit comprising:
a stable liquid pharmaceutical formulation set forth in claim 1; and
a container.

* * * * *